United States Patent
Melkent et al.

(10) Patent No.: US 8,845,737 B2
(45) Date of Patent: Sep. 30, 2014

(54) INTERBODY SPINAL IMPLANTS WITH EXTRAVERTEBRAL SUPPORT PLATES

(71) Applicant: Warsaw Orthopedic, Inc., Warsaw, IN (US)

(72) Inventors: Anthony J. Melkent, Memphis, TN (US); Brian Thoren, Collierville, TN (US); William Armstrong, Memphis, TN (US); Rajesh Remesh, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 13/905,723

(22) Filed: May 30, 2013

(65) Prior Publication Data

US 2013/0268080 A1 Oct. 10, 2013

Related U.S. Application Data

(62) Division of application No. 12/854,732, filed on Aug. 11, 2010, now Pat. No. 8,480,747.

(51) Int. Cl.
*A61F 2/44* (2006.01)
*A61F 2/46* (2006.01)
*A61F 2/30* (2006.01)

(52) U.S. Cl.
CPC ....... *A61F 2/442* (2013.01); *A61F 2002/30331* (2013.01); *A61F 2002/30383* (2013.01); *A61F 2/4455* (2013.01); *A61F 2002/30604* (2013.01); *A61F 2002/4475* (2013.01); *A61F 2002/30904* (2013.01); *A61F 2002/30517* (2013.01); *A61F 2/4611* (2013.01); *A61F 2/30965* (2013.01); *A61F 2002/30616* (2013.01); *A61F 2002/30841* (2013.01); *A61F 2002/30507* (2013.01); *A61F 2002/30578* (2013.01); *A61F 2/4684* (2013.01)
USPC ....................................... 623/17.16; 606/246

(58) Field of Classification Search
USPC ................. 606/89–91, 246; 623/17.11, 17.16
See application file for complete search history.

(56) References Cited

U.S. PATENT DOCUMENTS

| | | |
|---|---|---|
| 4,599,086 A | 7/1986 | Doty |
| 4,955,908 A | 9/1990 | Frey et al. |
| 5,192,327 A | 3/1993 | Brantigan |
| 5,290,312 A | 3/1994 | Kojimoto et al. |
| 5,364,399 A | 11/1994 | Lowery et al. |
| 5,397,364 A | 3/1995 | Kozak et al. |
| 5,405,391 A | 4/1995 | Hednerson et al. |
| 5,514,180 A | 5/1996 | Heggeness et al. |
| 5,888,223 A | 3/1999 | Bray, Jr. |

(Continued)

FOREIGN PATENT DOCUMENTS

WO  2007098288 A2  8/2007

*Primary Examiner* — Andrew Yang
*Assistant Examiner* — Olivia C Chang

(57) ABSTRACT

An implant assembly for a spinal column includes at least a plate and an interbody implant attached to the plate. The interbody implant is positioned in the spinal disc space and the plate extends extradiscally for attachment to the first and second vertebrae outside the disc space. The assembly may include recesses in the bottom surface of the plate, spacers, and spacing portions extending from the bottom surface of the plate that allow the plate to be secured to the interbody implant when the trailing end of the interbody implant is positioned in a recessed, flush or overhanging position relative to the laterally facing surfaces of the vertebrae.

12 Claims, 25 Drawing Sheets

(56) References Cited

U.S. PATENT DOCUMENTS

| | | |
|---|---|---|
| 5,916,267 A | 6/1999 | Tienboon |
| 6,066,175 A | 5/2000 | Henderson et al. |
| 6,096,080 A | 8/2000 | Nicholson et al. |
| 6,106,557 A | 8/2000 | Robioneck et al. |
| 6,120,503 A | 9/2000 | Michelson |
| 6,156,037 A | 12/2000 | LeHuec et al. |
| 6,159,211 A | 12/2000 | Boriani et al. |
| 6,228,085 B1 | 5/2001 | Theken et al. |
| 6,235,059 B1 | 5/2001 | Benezech et al. |
| 6,241,769 B1 | 6/2001 | Nicholson et al. |
| 6,342,074 B1 | 1/2002 | Simpson |
| 6,395,030 B1 | 5/2002 | Songer et al. |
| 6,432,106 B1 | 8/2002 | Fraser |
| 6,443,987 B1 | 9/2002 | Bryan |
| 6,461,359 B1 | 10/2002 | Tribus et al. |
| 6,485,517 B1 | 11/2002 | Michelson |
| 6,500,205 B1 | 12/2002 | Michelson |
| 6,500,206 B1 | 12/2002 | Bryan |
| 6,508,818 B2 | 1/2003 | Steiner et al. |
| 6,558,387 B2 | 5/2003 | Errico et al. |
| 6,558,423 B1 | 5/2003 | Michelson |
| 6,562,073 B2 | 5/2003 | Foley |
| 6,576,017 B2 | 6/2003 | Foley et al. |
| 6,579,290 B1 | 6/2003 | Hardcastle et al. |
| 6,629,998 B1 | 10/2003 | Lin |
| 6,635,087 B2 | 10/2003 | Angelucci et al. |
| 6,652,584 B2 | 11/2003 | Michelson |
| 6,682,561 B2 | 1/2004 | Songer et al. |
| 6,706,043 B2 | 3/2004 | Steiner et al. |
| 6,709,458 B2 | 3/2004 | Michelson |
| 6,716,247 B2 | 4/2004 | Michelson |
| 6,730,127 B2 | 5/2004 | Michelson |
| 6,733,531 B1 | 5/2004 | Trieu |
| 6,743,256 B2 | 6/2004 | Mason |
| 6,749,636 B2 | 6/2004 | Michelson |
| 6,770,096 B2 | 8/2004 | Bolger et al. |
| 6,793,679 B2 | 9/2004 | Michelson |
| 6,800,093 B2 | 10/2004 | Nicholson et al. |
| 6,808,537 B2 | 10/2004 | Michelson |
| 6,814,756 B1 | 11/2004 | Michelson |
| 6,843,804 B2 | 1/2005 | Bryan |
| 6,849,093 B2 | 2/2005 | Michelson |
| 6,890,355 B2 | 5/2005 | Michelson |
| 6,926,737 B2 | 8/2005 | Jackson |
| 6,962,606 B2 | 11/2005 | Michelson |
| 6,972,019 B2 | 12/2005 | Michelson |
| 6,972,035 B2 | 12/2005 | Michelson |
| 6,974,479 B2 | 12/2005 | Trieu |
| 6,984,234 B2 | 1/2006 | Bray |
| 6,987,136 B2 | 1/2006 | Erbe et al. |
| 6,989,031 B2 | 1/2006 | Michelson |
| 7,008,453 B1 | 3/2006 | Michelson |
| 7,033,394 B2 | 4/2006 | Michelson |
| 7,041,135 B2 | 5/2006 | Michelson |
| 7,077,864 B2 | 7/2006 | Byrd, III et al. |
| 7,112,222 B2 | 9/2006 | Fraser et al. |
| 7,118,598 B2 | 10/2006 | Michelson |
| 7,135,024 B2 | 11/2006 | Cook et al. |
| 7,135,043 B2 | 11/2006 | Nakahara et al. |
| 7,163,560 B2 | 1/2007 | Mason |
| 7,163,561 B2 | 1/2007 | Michelson |
| 7,172,627 B2 | 2/2007 | Fiere et al. |
| 7,229,441 B2 | 6/2007 | Trieu et al. |
| 7,232,464 B2 | 6/2007 | Mathieu et al. |
| 7,238,203 B2 | 7/2007 | Bagga et al. |
| 7,320,708 B1 | 1/2008 | Bernstein |
| 7,326,248 B2 | 2/2008 | Michelson |
| 7,338,525 B2 | 3/2008 | Ferree |
| 7,344,539 B2 | 3/2008 | Serhan et al. |
| 7,354,452 B2 | 4/2008 | Foley |
| 7,364,589 B2 | 4/2008 | Eisermann |
| 7,435,262 B2 | 10/2008 | Michelson |
| 7,442,209 B2 | 10/2008 | Michelson |
| 7,455,692 B2 | 11/2008 | Michelson |
| 7,540,882 B2 | 6/2009 | Michelson |
| 7,608,107 B2 | 10/2009 | Michelson |
| 7,611,536 B2 | 11/2009 | Michelson |
| 7,611,538 B2 | 11/2009 | Belliard et al. |
| 7,618,456 B2 | 11/2009 | Mathieu et al. |
| 7,621,957 B2 | 11/2009 | Errico et al. |
| 7,625,375 B2 | 12/2009 | Garden et al. |
| 7,637,951 B2 | 12/2009 | Michelson |
| 7,637,954 B2 | 12/2009 | Michelson |
| 2002/0004683 A1* | 1/2002 | Michelson ............... 623/17.16 |
| 2002/0111680 A1 | 8/2002 | Michelson |
| 2002/0193880 A1 | 12/2002 | Fraser |
| 2003/0187441 A1 | 10/2003 | Bolger et al. |
| 2003/0195632 A1 | 10/2003 | Foley et al. |
| 2004/0059419 A1 | 3/2004 | Michelson |
| 2004/0210226 A1 | 10/2004 | Trieu |
| 2004/0210310 A1 | 10/2004 | Trieu |
| 2004/0210313 A1 | 10/2004 | Michelson |
| 2005/0065608 A1 | 3/2005 | Michelson |
| 2005/0085913 A1 | 4/2005 | Fraser et al. |
| 2005/0101960 A1 | 5/2005 | Fiere et al. |
| 2005/0171606 A1 | 8/2005 | Michelson |
| 2005/0171607 A1 | 8/2005 | Michelson |
| 2005/0261774 A1 | 11/2005 | Trieu |
| 2005/0267578 A1 | 12/2005 | Michelson |
| 2006/0009845 A1 | 1/2006 | Chin |
| 2006/0009846 A1 | 1/2006 | Trieu et al. |
| 2006/0030851 A1 | 2/2006 | Bray et al. |
| 2006/0069442 A1 | 3/2006 | Michelson |
| 2006/0085071 A1 | 4/2006 | Lechmann et al. |
| 2006/0206208 A1 | 9/2006 | Michelson |
| 2007/0032871 A1 | 2/2007 | Michelson |
| 2007/0100340 A1 | 5/2007 | Lange |
| 2007/0106384 A1 | 5/2007 | Bray et al. |
| 2007/0106388 A1 | 5/2007 | Michelson |
| 2007/0123863 A1 | 5/2007 | Winslow |
| 2007/0270965 A1 | 11/2007 | Ferguson |
| 2007/0293948 A1 | 12/2007 | Bagga et al. |
| 2008/0021480 A1 | 1/2008 | Chin et al. |
| 2008/0051890 A1 | 2/2008 | Waugh et al. |
| 2008/0161855 A1 | 7/2008 | Serhan et al. |
| 2008/0161925 A1* | 7/2008 | Brittan et al. ............. 623/17.16 |
| 2008/0281425 A1 | 11/2008 | Thalgott et al. |
| 2009/0054987 A1 | 2/2009 | Chin et al. |
| 2009/0062921 A1 | 3/2009 | Michelson |
| 2009/0088849 A1 | 4/2009 | Armstrong et al. |
| 2009/0143862 A1 | 6/2009 | Trieu |
| 2009/0210064 A1 | 8/2009 | Lechmann et al. |
| 2009/0326580 A1* | 12/2009 | Anderson et al. ............. 606/246 |
| 2010/0057206 A1 | 3/2010 | Duffield et al. |

* cited by examiner

INTERBODY SPINAL IMPLANTS WITH EXTRAVERTEBRAL SUPPORT PLATES

CROSS-REFERENCE TO RELATED APPLICATION

This application is a divisional of co-pending application Ser. No. 12/854,732, filed on Aug. 11, 2010, which is herein incorporated by reference in its entirety.

BACKGROUND

The present invention relates generally to implant assemblies that include an interbody implant engaged to an extradiscal support plate, and to methods and systems for inserting one or more spinal implant assemblies with support plates.

Several techniques and systems have been developed for correcting and stabilizing the spine and for facilitating fusion at various levels of the spine. The spinal anatomy including the bony structure of vertebral bodies, vascular structures, neural structures, musculature, and other vital tissue along the spinal column make it difficult to position an interbody implant in the disc space between adjacent vertebral bodies or to engage a plate between the adjacent vertebrae. In addition, when an implant is placed into a disc space, the channel or path that the implant took to enter the disc space provides a path for retrograde movement of the implant from the disc space. The variability in the location of the trailing end of the implant relative to the adjacent vertebral bodies can make attaching a plate to the implant and to the adjacent vertebral bodies difficult to achieve.

Correction of deformities from approaches that parallel or extend substantially parallel to the sagittal plane is difficult to achieve with an interbody implant due to the intervening anatomy. Surface area contact between the implant and the hard cortical bone of the endplate can be too small so that the implant subsides too much and tends to want to break through the endplates. Unilateral fixation is not always an option because of stability issues of a narrow implant. While a lateral approach to the disc space avoids certain critical anatomical structures that impede access in other approaches, the ability to insert an implant through a small or minimally invasive portal and achieve the desired support in the disc space from a lateral approach is challenging. As a result, additional improvements in spinal fusion implants and insertion instruments and techniques are needed that make utilization of a lateral approach more palatable, although utilization of such implants and instrument is not necessarily limited to a lateral approach.

SUMMARY

According to one aspect, an implant assembly for a spinal column is disclosed that is capable of being inserted into a patient in a minimally invasive surgical approach. The implant assembly includes at least a plate and an interbody implant attached to the plate. The interbody implant is positioned in the spinal disc space and the plate extends extradiscally for attachment to the first and second vertebrae outside the disc space. Embodiments of the assembly include any one or combination of recesses in the bottom surface of the plate, spacers positioned against the bottom surface of the plate, or spacing portions extending from the bottom surface of the plate that allow the plate to be secured to the interbody implant when the trailing end of the interbody implant is positioned in a recessed, flush or overhanging position relative to the laterally facing surfaces of the vertebrae.

Related features, aspects, embodiments, objects and advantages of the present invention will be apparent from the following description.

DESCRIPTION OF THE ILLUSTRATED EMBODIMENTS

Figure 1:
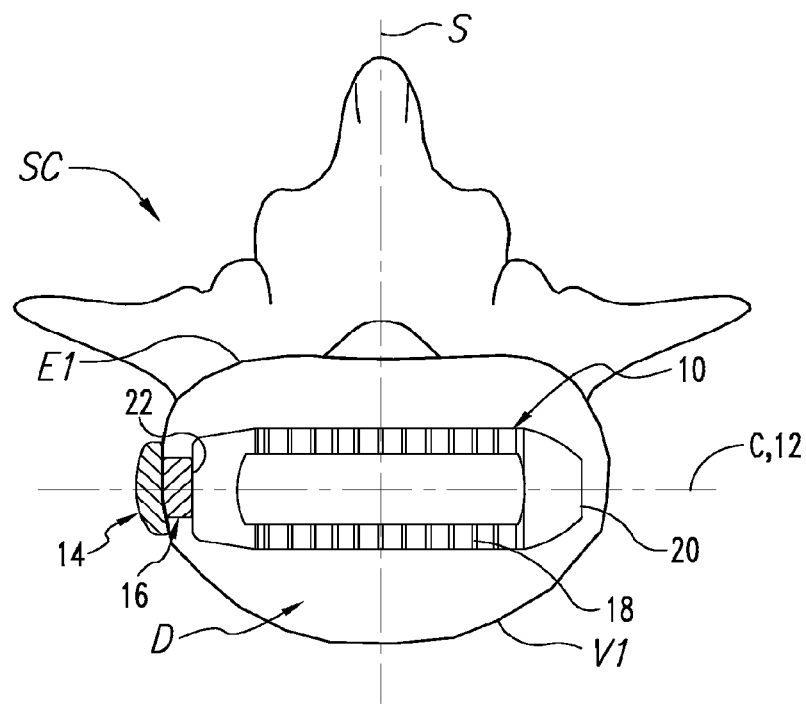
FIG. 1 is a diagrammatic plan view looking toward the axial plane of an endplate of a vertebral body of a spinal column with an interbody implant and plate engaged thereto.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and such further applications of the principles of the invention as illustrated herein are contemplated as would normally occur to one skilled in the art to which the invention relates.

Methods, techniques, instrumentation and implants are provided to restore and/or maintain a collapsed, partially collapsed, damaged, diseased, or otherwise impaired spinal disc space at a desired disc space height and adjacent endplate orientation. The instruments and implants may be used in techniques employing minimally invasive instruments and technology to access the disc space, although access in non-minimally invasive procedures is also contemplated. Access to the collapsed disc space can be uni-portal, bi-portal, or multi-portal. The instruments and implants may also be employed in a direct lateral approach to the spinal disc space, although other approaches are also contemplated, including antero-lateral, postero-lateral, oblique, posterior, and anterior approaches. Also, the surgical methods, techniques, instruments and implants may find application at all vertebral segments of the spine, including the lumbar, thoracic and cervical spinal regions.

Figure 2:
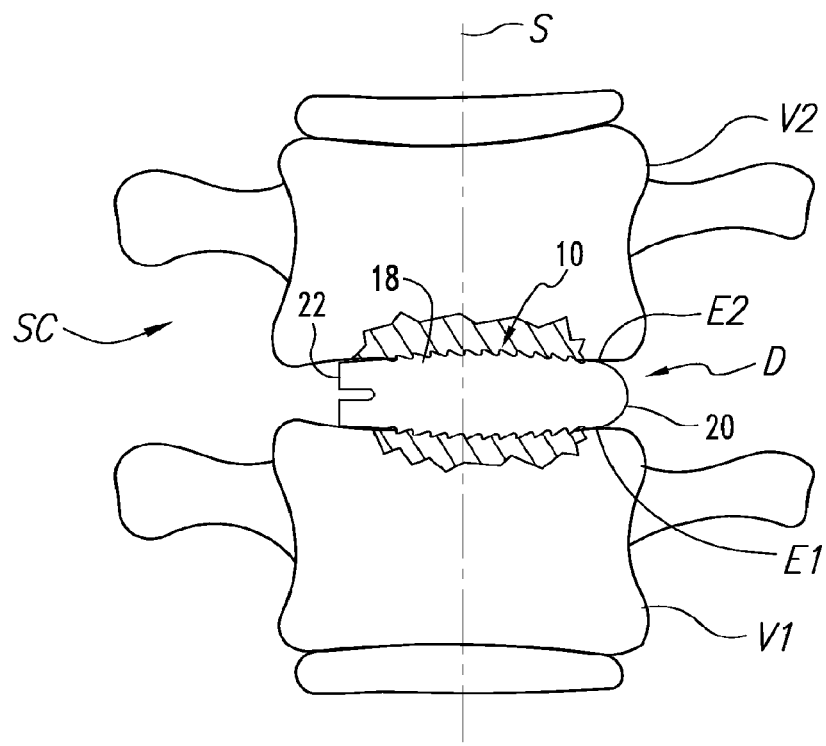
FIG. 2 is a diagrammatic elevation view looking toward the coronal plane at a vertebral level of the spinal column including the vertebral body and the interbody implant of FIG. 1 in a recessed position relative to the vertebrae.

FIG. 1 illustrates a plan view looking caudally toward the axial plane of a vertebral body V1. Spinal interbody implant 10 is positioned on the vertebral endplate E1 intradiscally between vertebral bodies V1, V2, and a plate 14 is attached to implant 10 so that plate 14 is secured extradiscally, or outside the disc space, to vertebral bodies V1, V2. Vertebral body V1, along with a second vertebral body V2 and disc space D, is further shown in an anterior view in FIGS. 2-4. Vertebral body V1 along with vertebral body V2 and spinal disc space D comprise a level of spinal column segment SC. Implant 10 is positioned in disc space D so its longitudinal axis 12 extends laterally across sagittal plane S and parallel to or generally parallel to coronal plane C. Implant 10 is positioned in disc space D between vertebral bodies V1 and V2 so that when it is in its implanted orientation it contacts endplates E1 and E2. Plate 14 is positioned so that it lies along the laterally facing surfaces of vertebral bodies V1, V2. According to one procedure, implant 10 is positioned into disc space D from a direct lateral approach DL. As used herein, a "direct lateral approach" is an approach that is parallel or substantially parallel to the coronal plane and thus orthogonal to or substantially orthogonal to the sagittal plane. The term "substantially parallel" means that the approach may vary up to 30 degrees from the parallel to the coronal plane. Other embodiments contemplate that implant 10 is positioned into disc space D from another approach, such as an anterior, posterior, or oblique approach.

Implant 10 comprises an elongate body 18 sized to fit within the disc space D between adjacent vertebral bodies V1, V2. Body 18 extends from a leading end 20 to an opposite trailing end 22. Leading end 20 can include a convexly rounded nose to facilitate insertion into disc space D and distraction of vertebral bodies V1, V2. Body 18 may also include superior and inferior bone engaging surfaces with teeth, ridges or other engagement structure to enhance engagement with the vertebral endplates. The bone engaging surfaces can be planar, convexly curved, tapered, or otherwise configured to be received between and contact at least a portion of endplates E1, E2 along at least a portion of the length of body 18. Body 18 may also include one or more cavities or openings through its superior and inferior bone engaging surfaces to facilitate bone growth through body 18. Body 18 also includes opposite side walls extending from leading 20 to trailing end 22, and also extending from the superior bone engaging surface to the inferior bone engaging surface. The side walls can be parallel to one another, or tapered relative to one another to converge or diverge toward the leading end 20. The side walls can be planar, concave or convex from leading end 20 to trailing end 22, concave or convex from the superior bone engaging surface to the inferior bone engaging surface, or combinations thereof.

Figure 3:
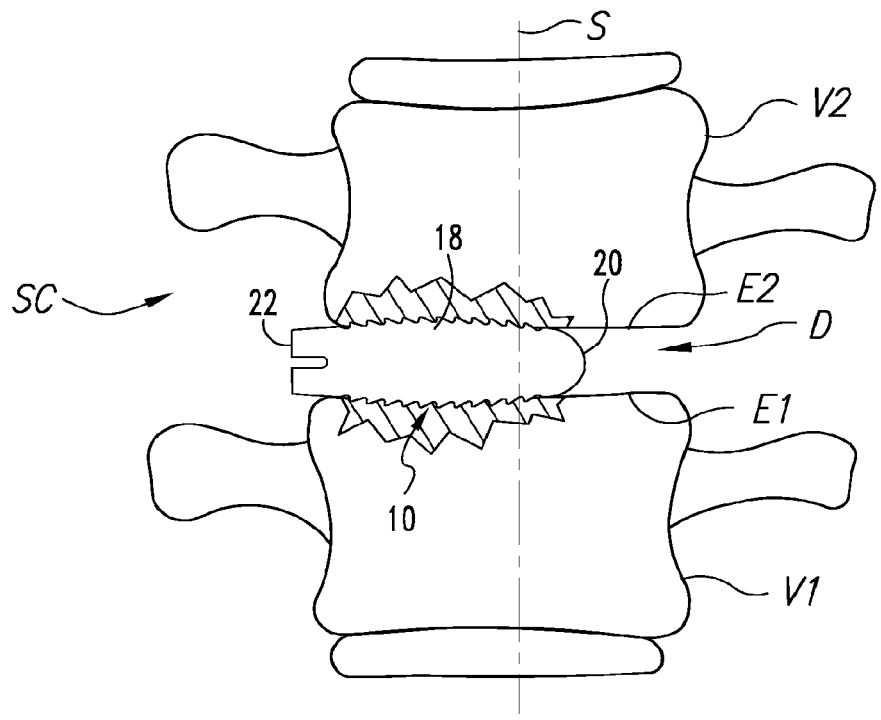
FIG. 3 is a diagrammatic elevation view looking toward the coronal plane at a vertebral level of the spinal column including the vertebral body and the interbody implant of FIG. 1 in an overhanging position relative to the vertebrae.
Figure 4:
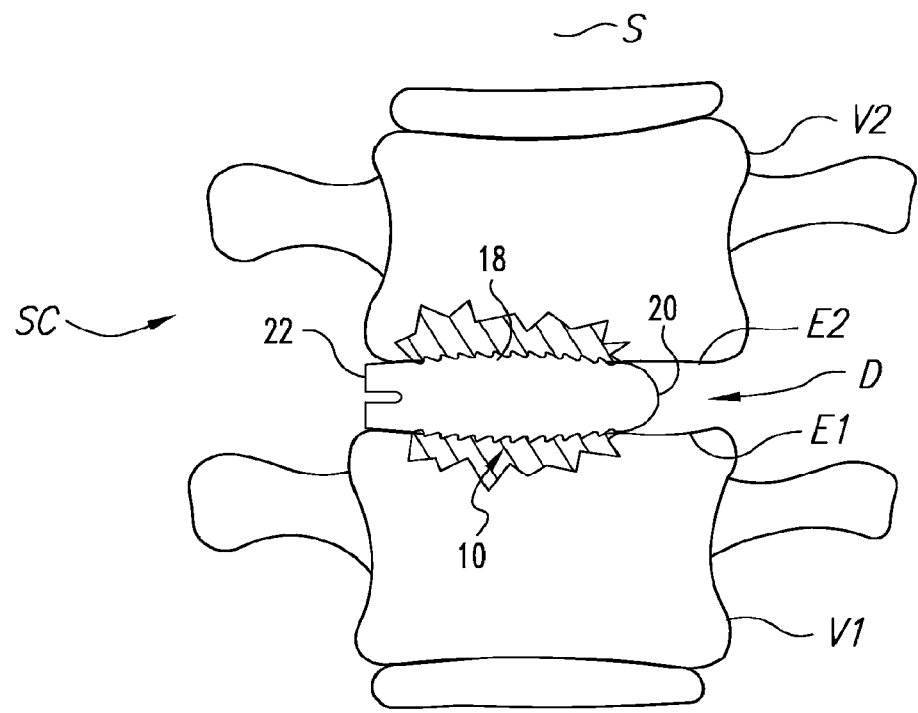
FIG. 4 is a diagrammatic elevation view looking toward the coronal plane at a vertebral level of the spinal column including the vertebral body and the interbody implant of FIG. 1 in a flush position relative to the vertebrae.

Implant 10 can be located in any one of a number of positions in disc space D when implanted. For example, leading end 20 can be advanced sufficiently into disc space D so that trailing end 22 is recessed into disc space D and offset from the laterally facing surfaces of vertebral bodies V1, V2. In order to provide a secure connection between plate 14 and implant 10, a spacer 16 is positioned between trailing end 22 and plate 14. Spacer 16 occupies the recessed area in disc space D so that body 18 and plate 14 abut facing distally and proximally facing surfaces, respectively, of spacer 16 to maximize the surface area contact and mechanically link one to the other. FIG. 3 shows another implantation location of implant 10 where trailing end 22 projects outwardly from the laterally facing surfaces of vertebral bodies V1, V2 in an overhanging condition relative to endplates E1, E2. As discussed further below, embodiments of plate 14 include a bottom surface facing disc space D with a recessed portion to receive the overhanging part of implant 10 including trailing end 22 while allowing the remaining portion of the bottom surface of plate 14 to be positioned flush against the laterally facing surfaces of vertebral bodies V1, V2, FIG. 4 shows another implantation location of implant 10 where trailing end 22 is flush with the laterally facing surfaces of vertebral bodies V1, V2. As discussed further below, embodiments of plate 14 include a bottom surface facing disc space D that is configured to abut the trailing end 22 of implant 10 either directly or with a spacer therebetween while allowing the remaining portion of the bottom surface of plate 14 to be positioned flush against the laterally facing surfaces of vertebral bodies V1, V2.

Figure 5:
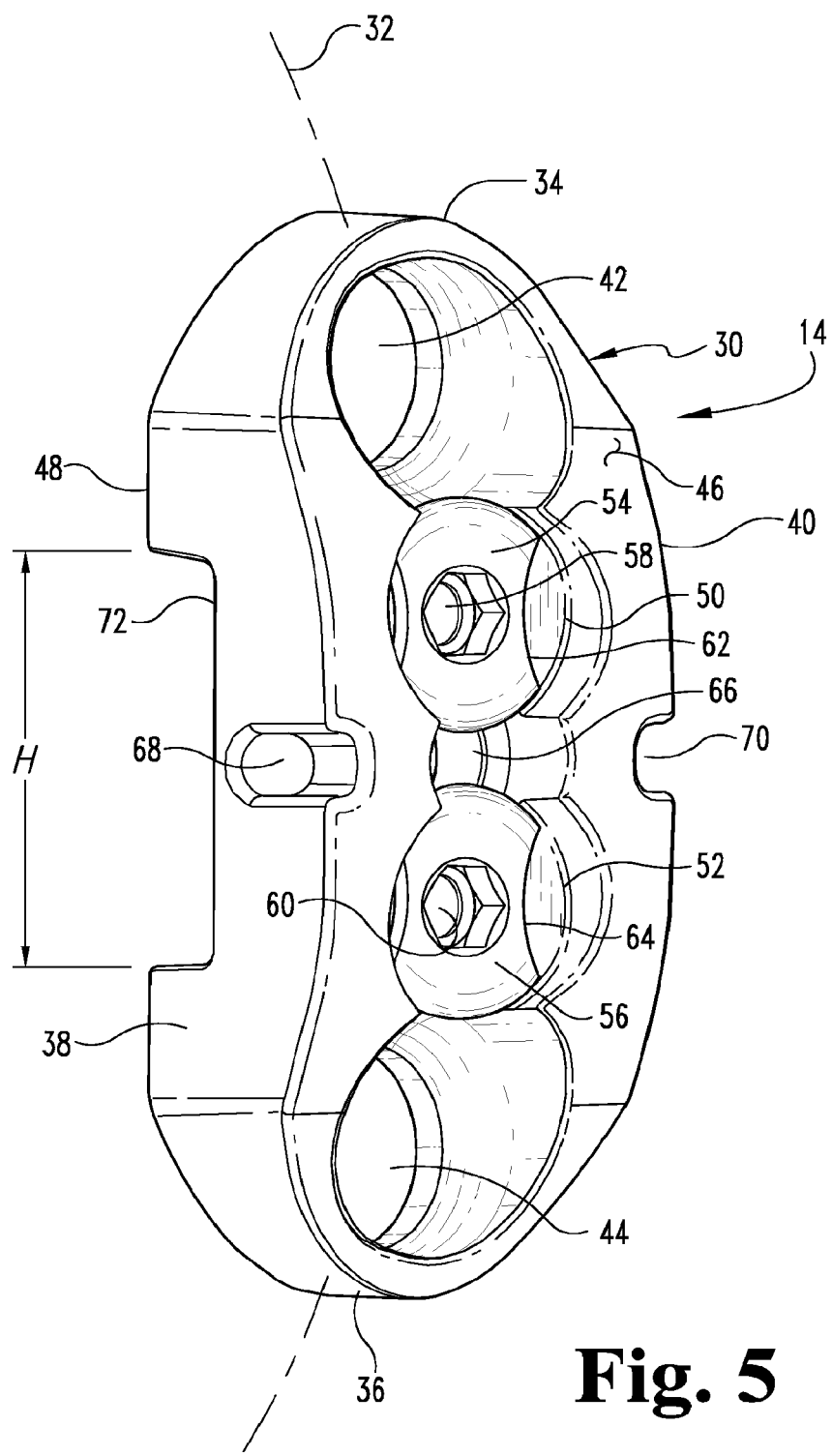
FIG. 5 is a perspective front view of a plate attachable to an interbody implant.
Figure 6:
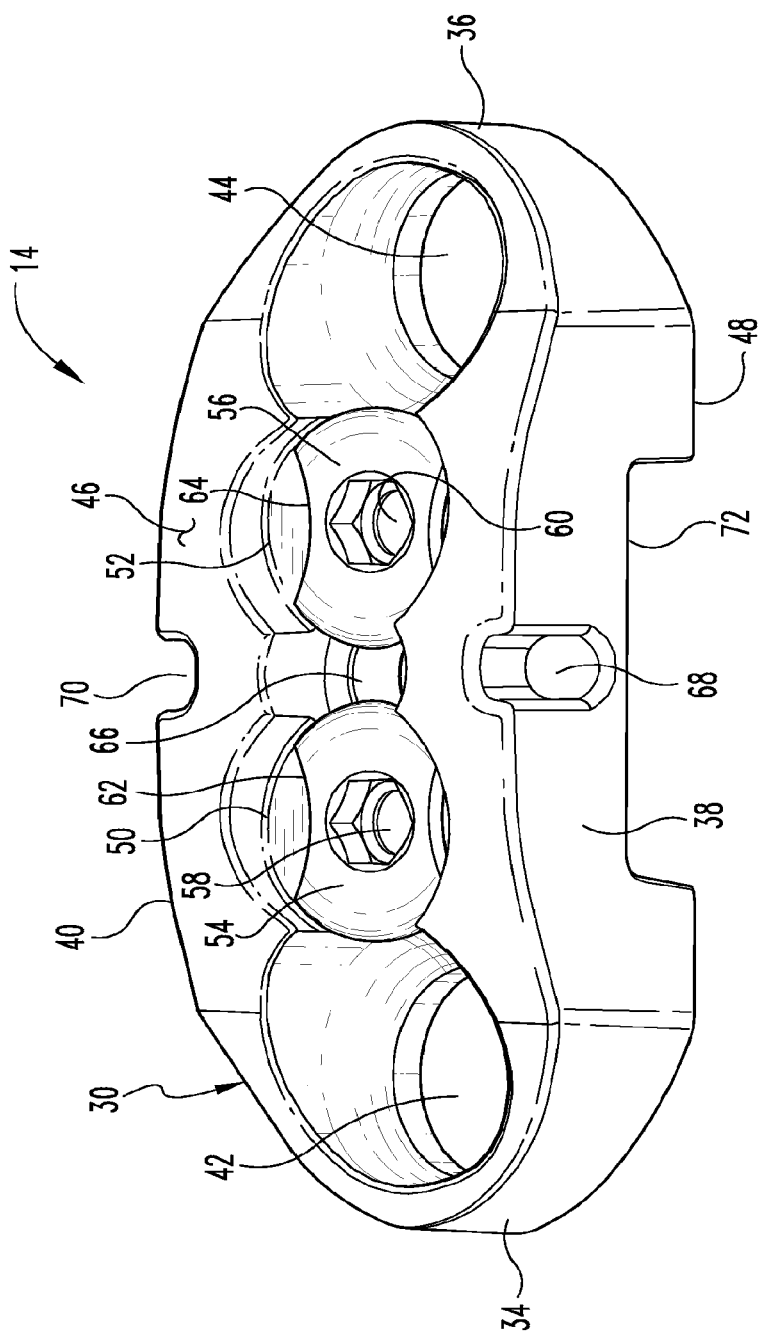
FIG. 6 is another perspective view of the plate of FIG. 5.

Further details regarding one embodiment of the plate 14 are shown in FIGS. 5-6. Plate 14 includes an elongated body 30 that extends along a longitudinal axis 32 that is oriented to extend along the central axis of the spinal column and between vertebral bodies V1, V2 when plate 14 implanted. Body 30 includes an upper or cephalad end 34 and an opposite lower or caudal end 36. Body 30 also includes opposite side surfaces 38, 40 that extend between ends 34, 36. Ends 34, 36 are convexly rounded between side surfaces 38, 40 to reduce the profile of body 30. Body 30 also includes a superior bone screw hole 42 adjacent upper end 34 and an inferior bone screw hole 44 adjacent lower end 36. Bone screw holes 42, 44 extend through and open at top surface 46 and bottom surface 48 of body 30.

Body 30 also includes a first recess 50 adjacent to bone screw hole 42 and a second recess 52 adjacent to bone screw hole 44. A central bore 66 extends through the center of body 30 between recesses 50, 52. Recesses 50, 52 extend into top surface 46 and house respective ones of a first retaining element 54 and a second retaining element 56. Retaining elements 54, 56 can be secured to body 30 in the respective recess 50, 52 with a threaded shaft, clip or other configuration that allows the retaining elements 54, 56 to rotate while attached to body 30. Retaining elements 54, 56 each include a circular head that defines a central driving tool receptacle 58, 60, respectively. The circular heads include opposite concavely curved sidewall portions 62, 64 that can be aligned simultaneously with the respective adjacent bone screw hole 42, 44 and central bore 66 to allow insertion of a bone screw and its proximal head into the adjacent hole 42, 44 and a fastener into central bore 66. When the bone screw heads are seated in holes 42, 44, retaining elements 54, 56 can be rotated so that the convexly curved portion of its head overlaps the respective hole 42, 44 and blocks or contacts the bone screw head to prevent bone screw back-out from holes 42, 44 and also to overlap central bore 66 to block or prevent back-out of the fastener positioned therein.

Body 30 of plate 14 also includes grooves 68, 70 on opposite sides of body 30 that extend into side surfaces 38, 40 from top surface 46, but stop short of bottom surface 48. As discussed further below, grooves 68, 70 receive tines from an inserter instrument. In addition, bottom surface 48 of body 30 includes a notch 72 that recesses the central portion of bottom surface 48 relative to the portions of bottom surface 48 that extend around bone screw holes 42, 44. Notch 72 extends through the opposite side surfaces 38, 40, and central bore 66 opens through notch 72. The height H of notch 72 along longitudinal axis 32 is at least as great as the height of implant 10 at trailing end 22. In addition, notch 72 offsets the portion of bottom surface 48 defined thereby proximally from the portions of bottom surface 48 extending around holes 42, 44 to provide the desired fit with an overhanging implant 10. The portions of bottom surface 48 around bone screw holes 42, 44 are offset distally from the recessed surface in notch 72, and define a concavely curved surface profile along central longitudinal axis 32 to fit with the anatomy along the laterally facing surfaces of vertebrae V1, V2. Top surface 46 defines a convexly curved profile along central longitudinal axis 32 from upper end 34 to lower end 36 to provide a smooth, low profile arrangement for body 30 that projects from vertebral bodies V1, V2.

Figure 7:
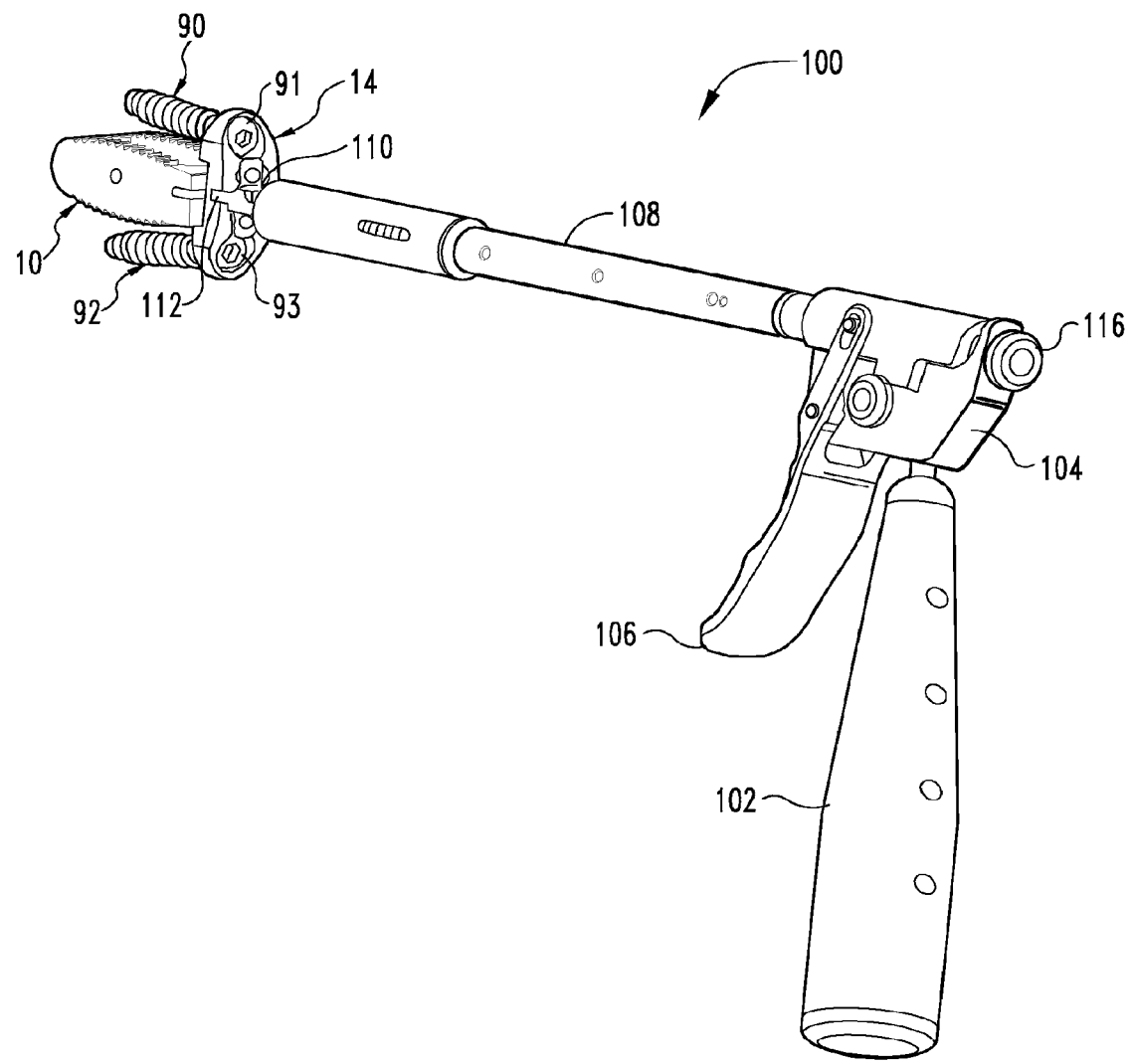
FIG. 7 is a perspective view of the plate of FIG. 5 attached to an interbody implant and inserter.
Figure 8:
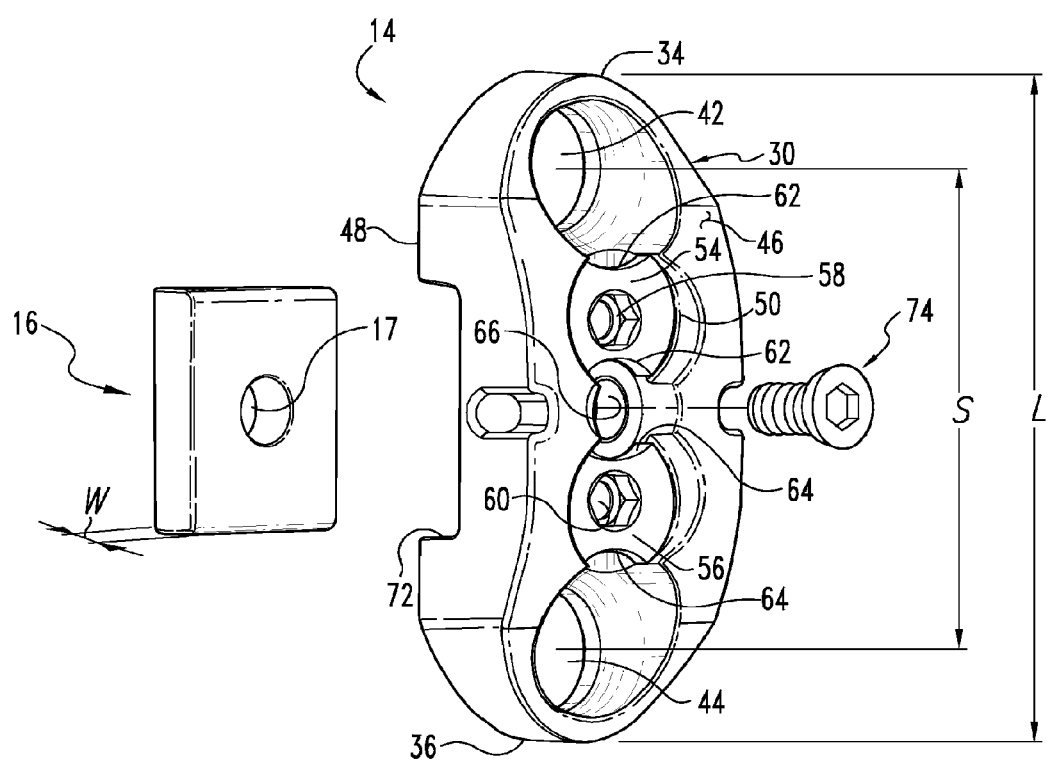
FIG. 8 is an exploded perspective rear view of the plate along with an optional spacer for positioning between the plate and the interbody implant.

Referring now to FIG. 7, there is shown interbody implant 10 directly engaged to plate 14, and an inserter 100 directly engaged to plate 14. Plate 14 includes first and second bone engaging fasteners 90, 92 extending through respective ones of the holes 42, 44. Bone engaging fasteners 90, 92 are shown as bone screws with a threaded shaft projecting from bottom surface 48 to engage respective ones of the vertebrae V1, V2 and heads 91, 93 that are received in counterbores in top surface 46 extending around respective ones of the bone screw holes 42, 44. Plate 14 is attached to interbody implant with a fastener 74 (FIG. 8) that extends through central bore 66 and into a hole in implant 10 that is threaded or otherwise configured to engage fastener 74. In addition, an optional spacer 16 can be provided in notch 72 of plate 14 if implant 10 is positioned in a recessed or flush condition relative to vertebral bodies V1, V2. If implant 10 is positioned in an overhang position, spacer 14 can be omitted and the trailing end 22 of implant 10 can be received directly into notch 72 of plate 14. Providing spacers 16 of various widths W and notch 72 allows the same plate 14 and implant 10 to be used regardless of the position of trailing end 22 of implant 10 in disc space D.

In one embodiment, inserter instrument 100 includes a proximal actuating structure that is activated by the surgeon or other user to manipulate a distal grasping portion to engage and hold the plate and interbody implant together for insertion into the patient as an implant assembly. The actuating structure includes a pistol-grip type arrangement with a handle 102 extending from a mounting structure 104 and a trigger 106 pivotally coupled to mounting structure 104. Inserter 100 also includes an outer sleeve 108 slidably mounted to and extending distally from mounting structure 104. Sleeve 108 is pivotally coupled at its proximal end to trigger 106, and is movably longitudinally by moving trigger 106 toward handle 102. Inserter 100 also houses an inner rod with a grasping assembly 110 at its distal end. Grasping assembly 110 includes a pair of tines 112 extending distally from sleeve 108 that are spaced from one another for positioning in grooves 68, 70 of plate 14. Sleeve 108 translates distally along grasping assembly 110 to bias tines 112 toward one another and grip plate 14 between tines 112. The inner rod includes a proximal knob 116 adjacent to mounting structure 104 to allow manipulation of the rod in sleeve 108, and to receive impaction forces to facilitate insertion of implant 10 into disc space D.

When assembled as shown in FIG. 7, inserter 100 holds plate 14, and plate 14 is engaged to implant 10 with fastener 74. Various spacers 16 can be provided in differing widths W to accommodate situations in which implant 10 is to be positioned in a flush or recessed positioned relative to vertebrae V1, V2 in disc space D. Spacer 16 includes a central hole 17 to allow passage of fastener 74 therethrough and into implant 10. Pre-operative planning and/or trial insertion of a spacer and plate assembly can be employed to determine whether or not a spacer 16 is to be employed and, if so, what width of spacer 16 to employ.

Since the plate and interbody implant can be held together prior to insertion and implanted with inserter 100, the entire plate and implant assembly can be inserted into the patient together in a minimally invasive surgical approach. For example, a tubular retractor, retractor blades, or other retraction device can be employed to maintain a pathway through skin and tissue of the patient to disc space D. In one particular embodiment, this pathway has a cross-sectional dimension of about 30 millimeters, and a length dimension ranging from about 90 millimeters to about 150 millimeters extending from the lateral faces of vertebrae V1, V2 to the proximal end opening of the pathway into the patient. In this particular embodiment, plate 14 is provided with a length L from upper end 34 to lower end 36 sized to pass through the 30 millimeter opening provided by the pathway while implant 10 is engaged to plate 14. This allows the centers of holes 42, 44 to be spaced from one another a distance S, ranging from about 12 millimeters to about 20 millimeters. The relative close spacing of holes 42, 44 provides screw angles through the plate 14 that allow bone screws 90, 92 to be inserted through the minimally invasive pathway and driven into the vertebrae V1, V2 so that bone screws 90, 92 angularly diverge from one another in the cephalad and caudal directions from bottom surface 48 of plate 14. In one embodiment, the screws are inserted at an angle ranging from about 5 degrees to about 10 degrees relative to the axial plane of spinal column segment SC. Other embodiments contemplate screw angles relative to the axial plane that range from 0 degrees to about 30 degrees.

Figure 9:
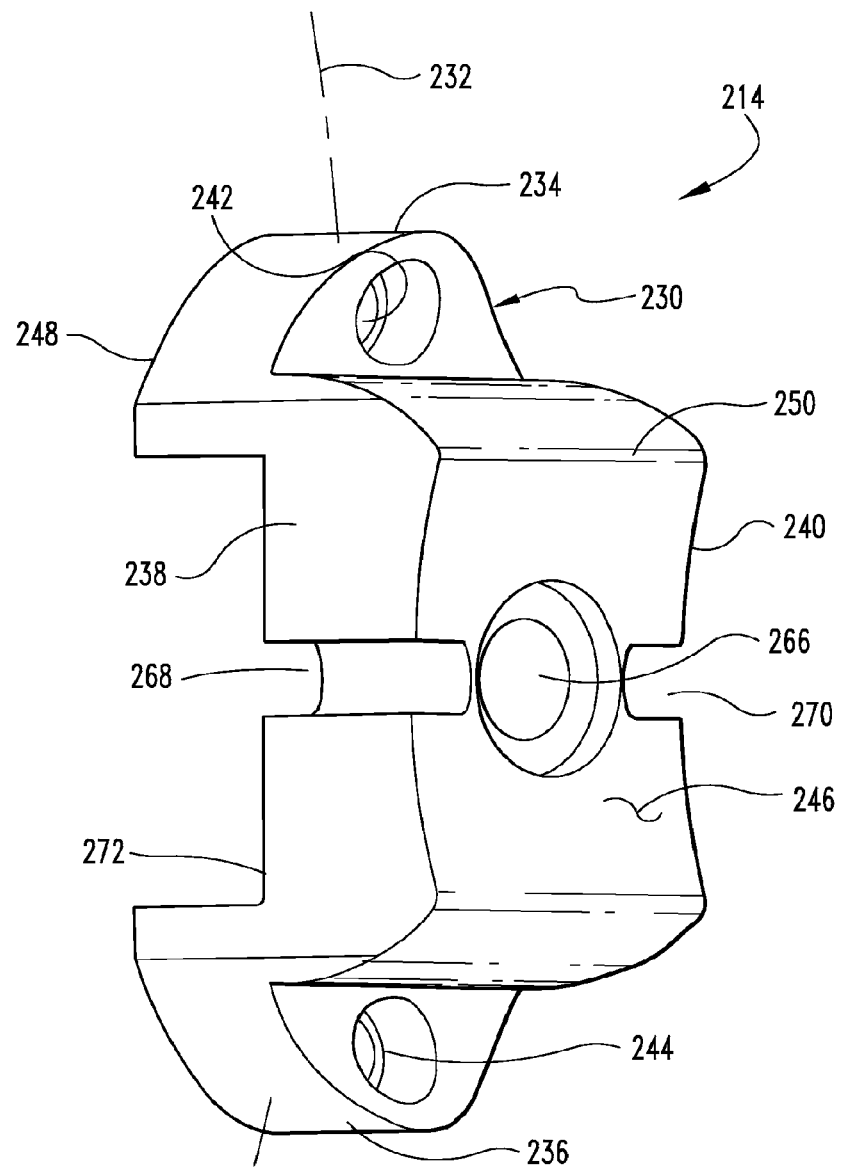
FIG. 9 is a perspective view of another embodiment plate.

Referring to FIG. 9, there is shown another embodiment plate designated at 214. Plate 214 is similar to plate 14 discussed above in that it is attached to implant 10 either directly or with a spacer between the implant and plate. Plate 214 includes grooves 268, 270 in side surfaces 238, 240 that extend through top surface 246 and through bottom surface 248 at notch 272. Plate 214 also lacks retaining element recesses in top surface 246, and top surface 246 is concavely curved along central longitudinal axis 232 from upper end 234 to lower end 236. The concave curvature allows an increase in the angulation of the bone screws relative to the axial plane when inserted into the plate holes 242, 244 through the minimally invasive pathway. In addition, body 230 of plate 214 includes a central hub 250 projecting proximally outwardly that is aligned with notch 272. Central bore 266 and grooves 268, 270 are formed through central hub 250.

Figure 10:
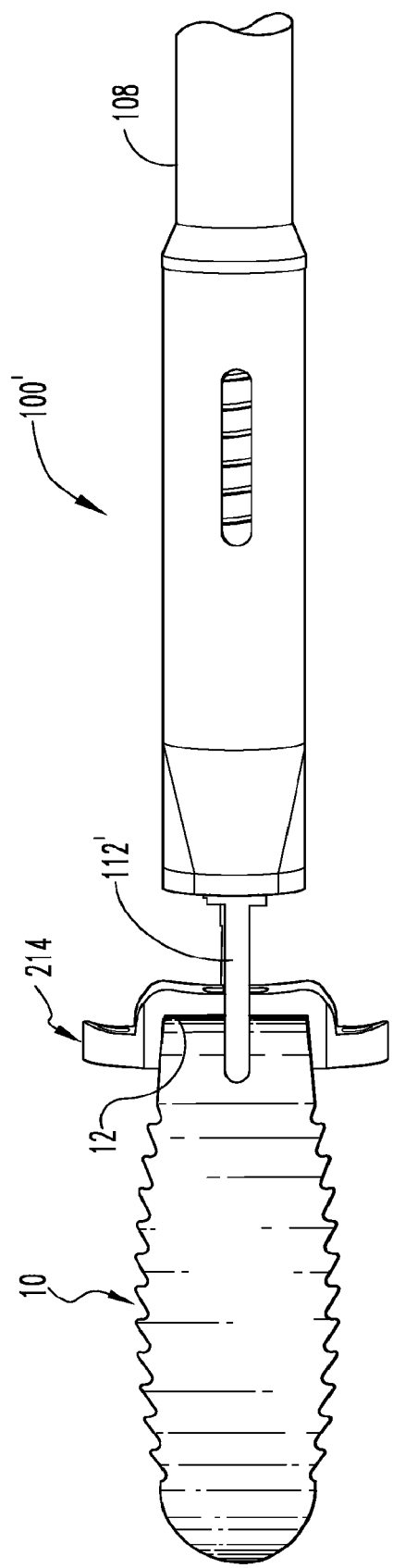
FIG. 10 is an elevation view of the plate of FIG. 9 attached between an interbody implant and an inserter.

Referring to FIG. 10, plate 214 and implant 10 are engaged to one another, and engaged to a modified inserter 100'. Inserter 100' is similar to inserter 100 discussed above, but includes longer tines 112' that extend through grooves 268, 270 and into aligned grooves 15 formed in the sides of implant 10 to facilitate insertion of the plate and implant assembly together into the patient. Notch 272 receives trailing end 22 of implant 10 so that implant 10 can be positioned in disc space D in an overhang condition while bottom surface 248 of plate 214 is aligned with the laterally facing outer surfaces of vertebral bodies V1, V2.

Figure 12:
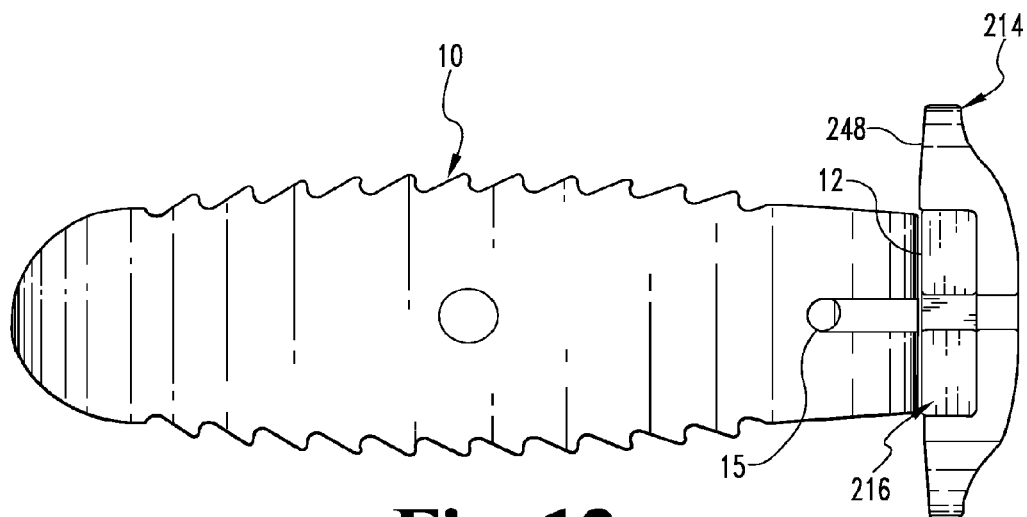
FIG. 12 is an elevation view of the plate of FIG. 9 and the spacer of FIG. 11 engaged to an interbody implant to form an implant assembly.
Figure 11:
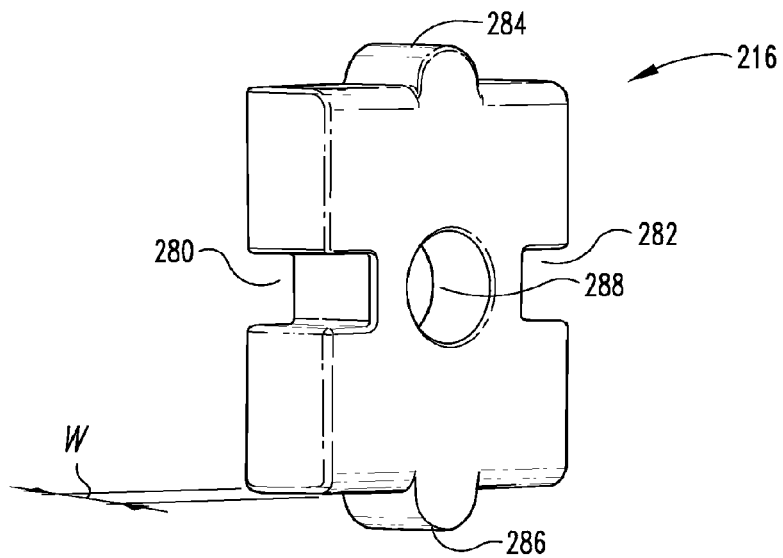
FIG. 11 is a perspective view of another embodiment spacer.
Figure 13:
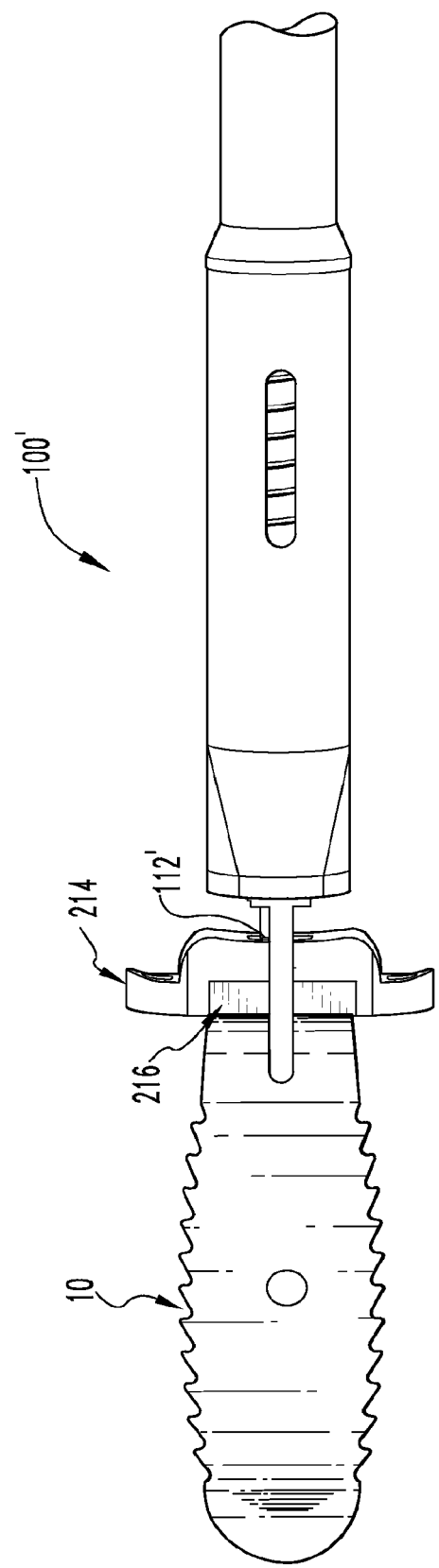
FIG. 13 is an elevation view of the inserter engaged to the implant assembly of FIG. 12.

FIGS. 11-13 show plate 214 with one embodiment of a spacer 216 that spaces the portion of bottom surface 248 along notch 272 of body 230 from trailing end 22 of implant 10, as shown in FIG. 12. Spacer 216 includes a rectangular body with notches 280, 282 formed in opposite sides thereof to receiver tines 112' from inserter 100', as shown in FIG. 13. In this embodiment, width W of spacer 216 is sized so that bottom surface 248 of body 230 around holes 242, 244 is aligned with trailing 22 of implant 10 when implant 10 is positioned in a flush position relative to the vertebral bodies V1, V2. Spacer 216 provides an interface between plate 214 and implant 10 and aligns the portions of bottom surface 248 around holes 242, 244 with the laterally facing surfaces of vertebral bodies V1, V2. In addition, spacer 216 includes upper and lower nubs 284, 286 that are received in correspondingly shaped recesses (not shown) formed in plate 214 at notch 272 to prevent spacer 216 from rotating relative to plate 214 as spacer 216 is engaged to plate 214 and implant 10 with a fastener through hole 288.

Figure 15:
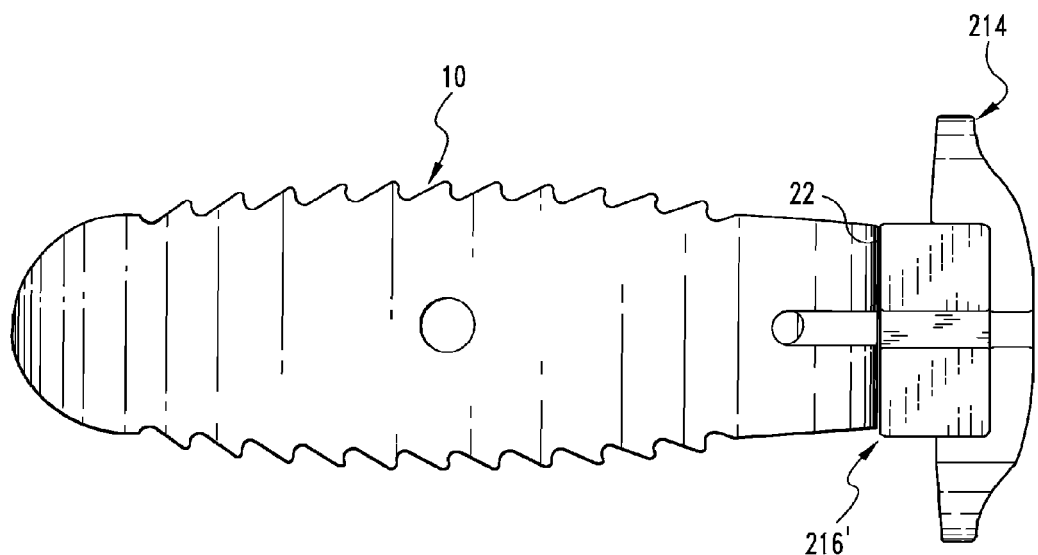
FIG. 15 is an elevation view of the plate of FIG. 9 and the spacer of FIG. 14 engaged to an interbody implant to form an implant assembly.
Figure 14:
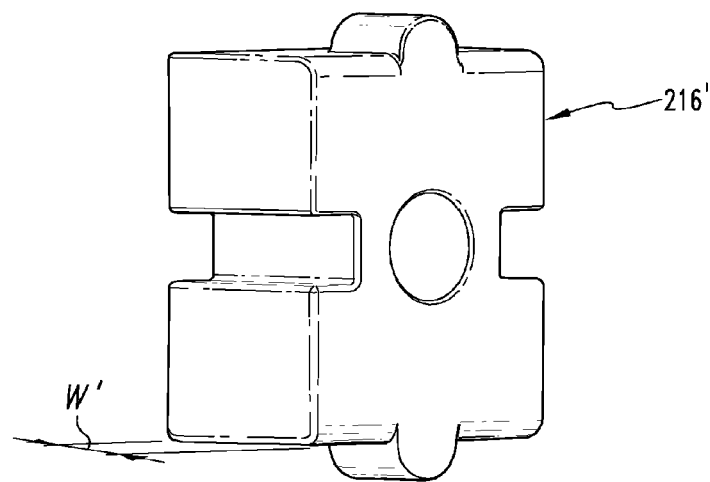
FIG. 14 is a perspective view of another embodiment spacer.
Figure 16:
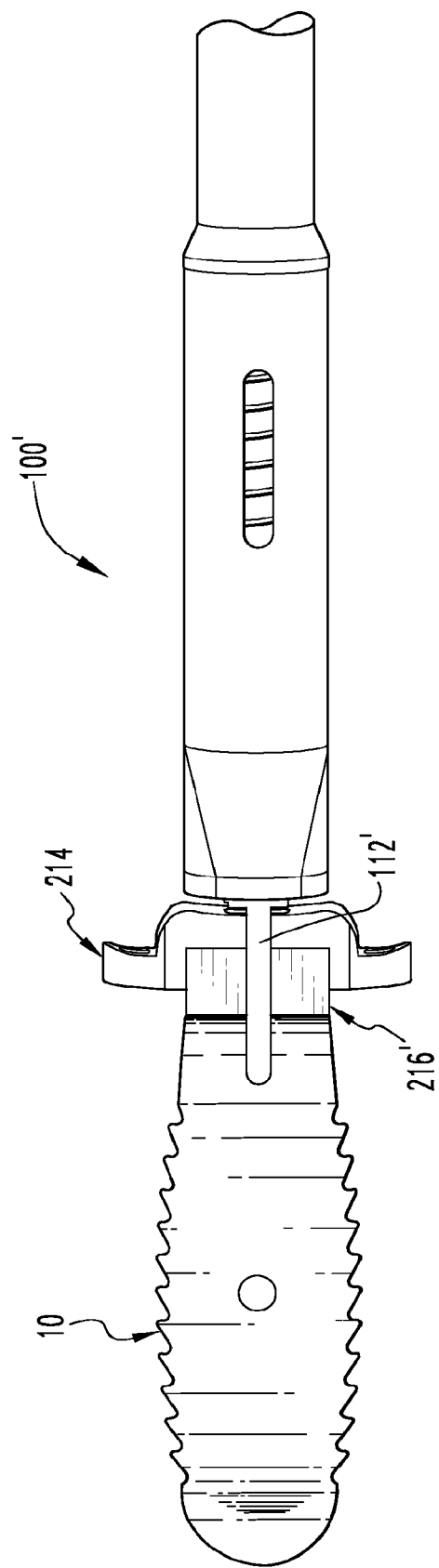
FIG. 16 is an elevation view of the inserter engaged to the implant assembly of FIG. 15.

Referring to FIGS. 14-16, another embodiment spacer 216' is shown that is identical to spacer 216, but includes a width W' that is greater than width W of spacer 216. Spacer 216' can be employed in procedures where implant 10 is positioned in disc space D with its trailing end 22 recessed into disc space D relative to the laterally facing surfaces of vertebral bodies V1, V2. The greater width W' locates the portions of the bottom surface of plate 214 around holes 242, 244 flush against the laterally facing surfaces of vertebral bodies V1, V2 while providing a mechanical link between implant 10 and plate 214.

Figure 18:
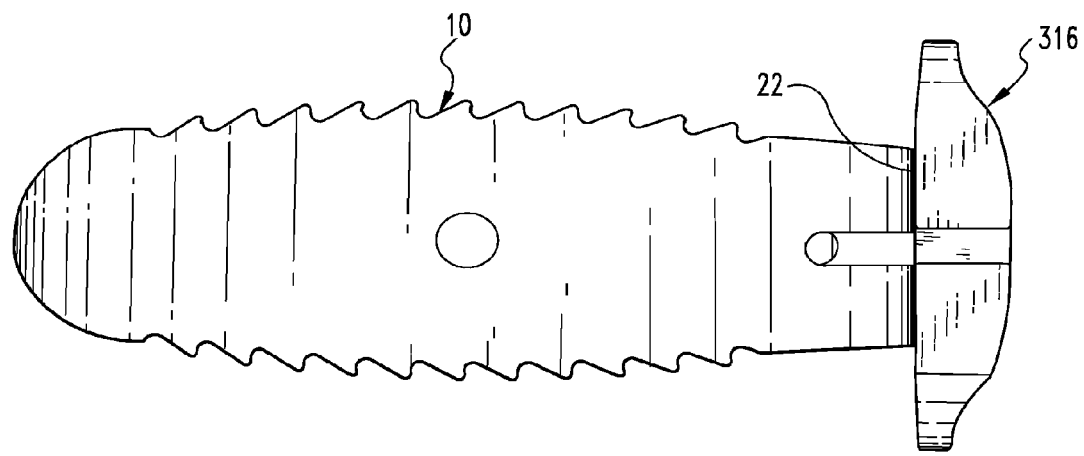
FIG. 18 is an elevation view of the plate of FIG. 17 attached to an interbody implant.
Figure 17:
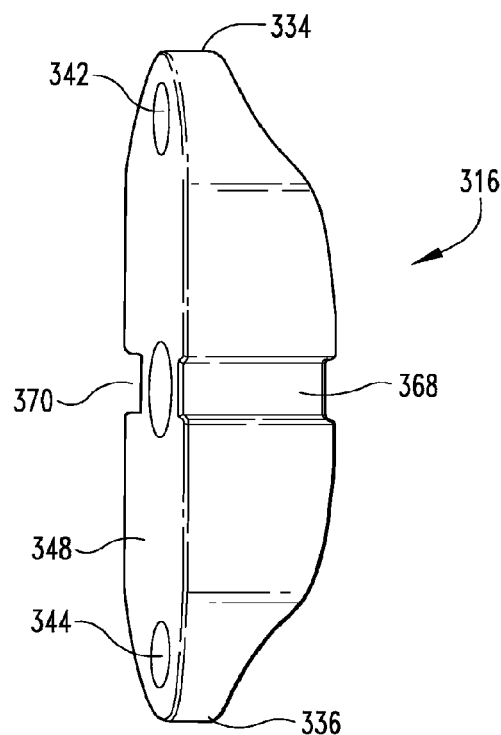
FIG. 17 is a perspective view of another embodiment plate.
Figure 20:
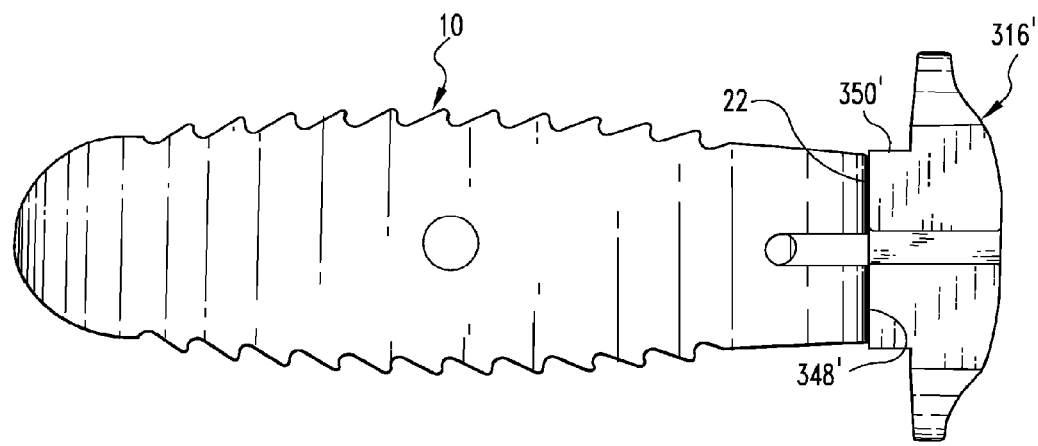
FIG. 20 is an elevation view of the plate of FIG. 19 attached to an interbody implant.
Figure 19:
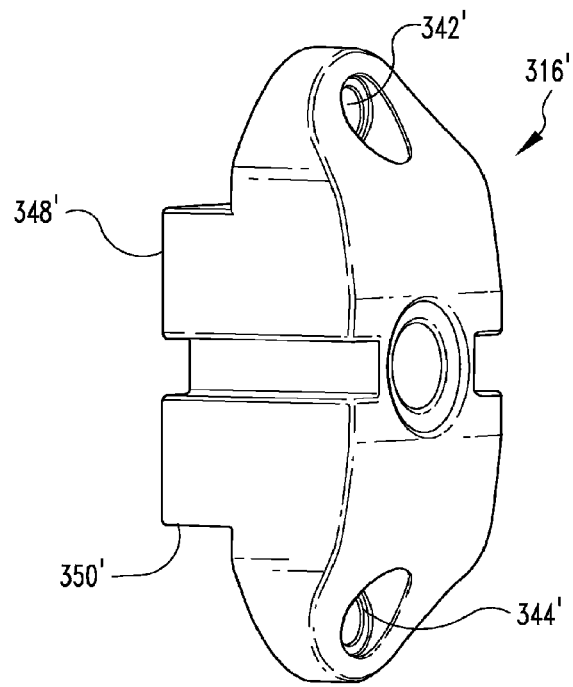
FIG. 19 is a perspective view of another embodiment plate.

Referring to FIGS. 17-18, another embodiment plate 316 is shown that lacks a notch in its bottom surface, but includes a substantially planar bottom surface 348 extending between upper and lower ends 334, 336. Bottom surface 348 is positioned in abutting engagement with trailing end 22 of implant 10. Plate 316 also includes grooves 368, 370 in its opposite side surfaces to receive tines from an inserter. Plate 316 is employed in arrangements where trailing end 22 is flush with the laterally facing surfaces of vertebral bodies V1, V2 so that the portions of bottom surface 348 around holes 342, 344 are positioned against the laterally facing surfaces of vertebral bodies V1, V2. In another embodiment, a plate 316' is shown in FIGS. 19-20 that is similar to plate 316, but plate 316' includes a bottom surface 348' formed at least in part by a spacer that is defined by a monolithic projecting portion 350' that extends distally outwardly from the portions of bottom surface 348' around holes 342', 344'. This embodiment is employed when implant 10 is positioned in disc space D with trailing end 22 recessed into the disc space from the laterally facing surfaces of vertebral bodies V1, V2.

Figure 22:
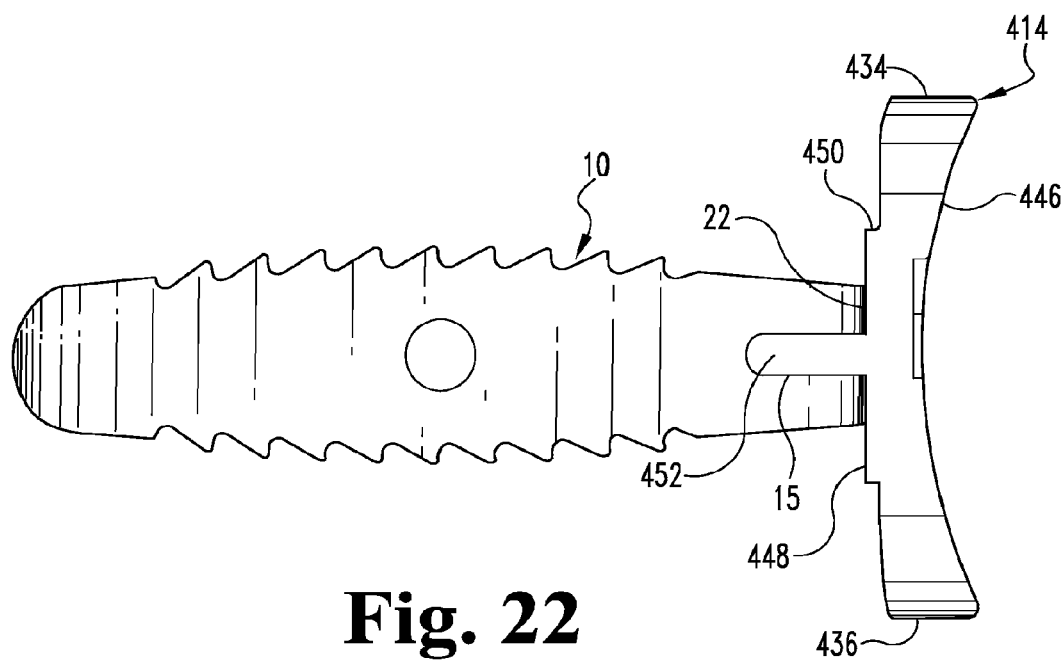
FIG. 22 is an elevation view of the plate of FIG. 21 attached to an interbody implant.
Figure 21:
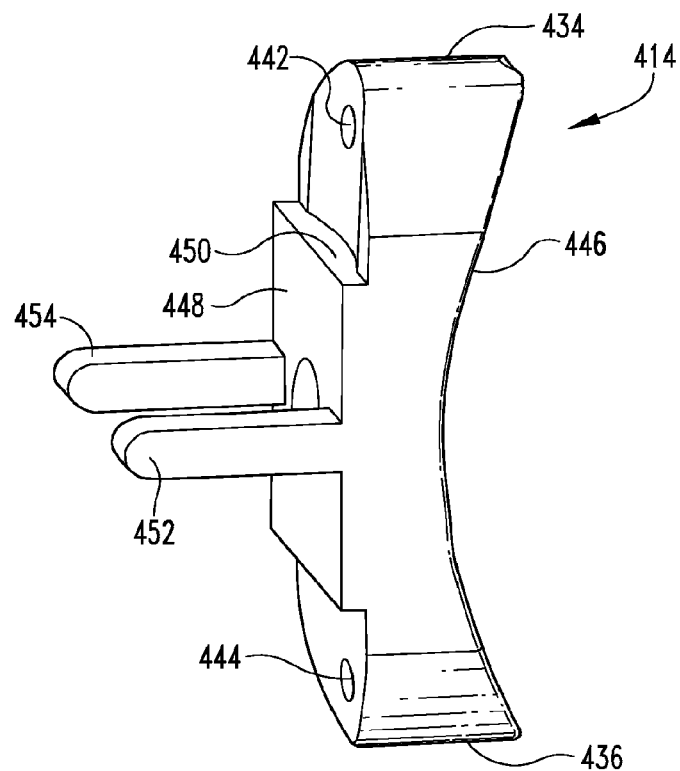
FIG. 21 is a perspective view of another embodiment plate.

FIGS. 21-26 show additional embodiments of a plate for engagement to implant 10 at various positions of trailing end 22 of implant 10 in the disc space D. In FIG. 21, plate 414 includes a body with a top surface 446 that is concavely curved from upper end 434 to lower end 436. Plate 414 also includes a bottom surface 448 with portions extending around holes 442, 444 and a spacer formed by a monolithic outwardly projecting portion 450 between holes 442, 444. The spacer portion of bottom surface 448 along projecting portion 450 is positioned in abutting contact with trailing end 22 of implant 10. In addition, plate 414 includes opposite tines 452, 454 extending outwardly from bottom surface 448 that are received in grooves 15 formed in the sides of implant 10, as shown in FIG. 22. The projecting portion 450 allows plate 414 to contact trailing end 22 of implant 10 when trailing end 22 is positioned in a recessed position in disc space D.

Figure 24:
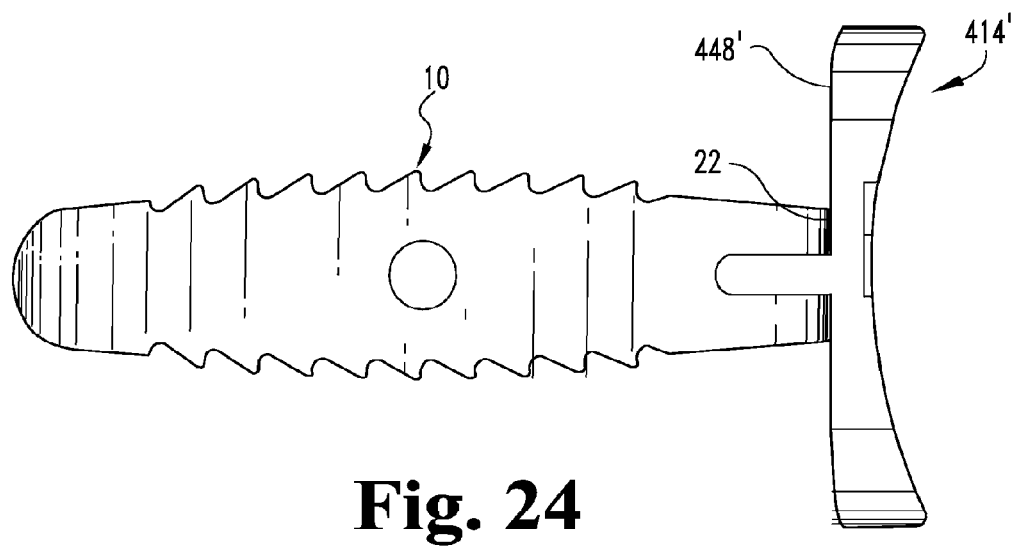
FIG. 24 is an elevation view of the plate of FIG. 23 attached to an interbody implant.
Figure 23:
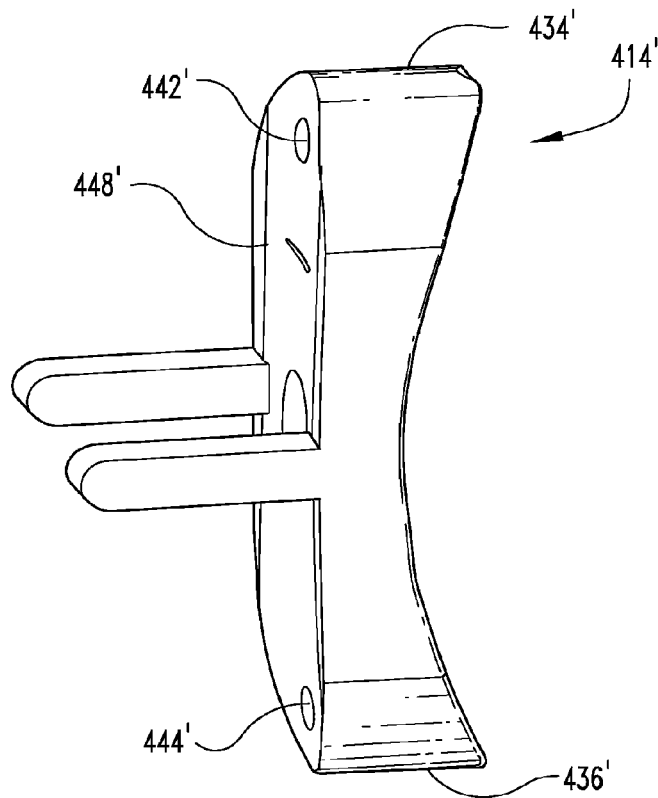
FIG. 23 is a perspective view of another embodiment plate.

FIG. 23 shows another embodiment of plate 414, designated as plate 414', in which there is no projecting portion 450 so that bottom surface 448' is planar or substantially planar from upper end 434' to lower end 436'. This positions the portion of bottom surface 448' in contact with trailing end 22 of implant 10 in substantially the same plane as the portion of bottom surface 448' around holes 442', 444', as shown in FIG. 24. Thus, plate 414' is employed in procedures where trailing end 22 of implant 10 is positioned flush with the laterally facing surfaces of vertebral bodies V1, V2.

Figure 26:
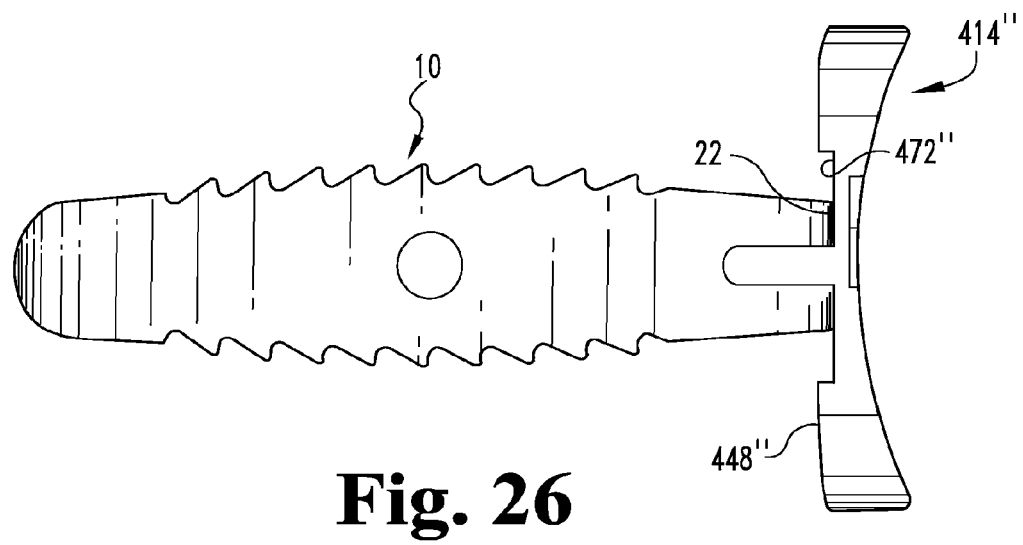
FIG. 26 is an elevation view of the plate of FIG. 25 attached to an interbody implant.
Figure 25:
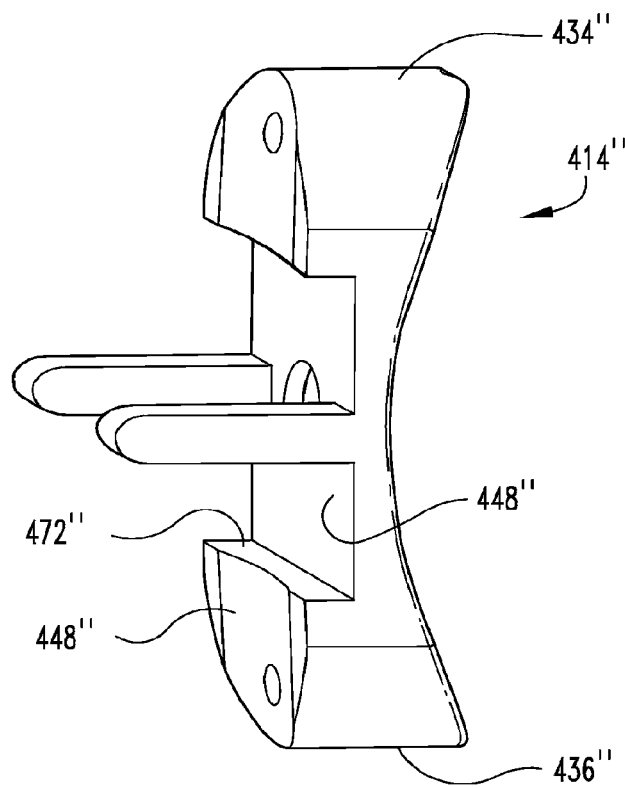
FIG. 25 is a perspective view of another embodiment plate.

FIG. 25 shows another embodiment of plate 414, designated as plate 414", in which there is no projecting portion 450 but a notch 472" forming a recess in bottom surface 448". Notch 472" recesses the portion of bottom surface 448" that contacts trailing end 22 of implant 10 from the portions of bottom surface 448" at upper end 434" and lower end 436", as shown in FIG. 26. Thus, plate 414" is employed in procedures where implant 10 is positioned with trailing end 22 in overhanging relation to the laterally facing surfaces of vertebral bodies V1, V2.

Figure 28:
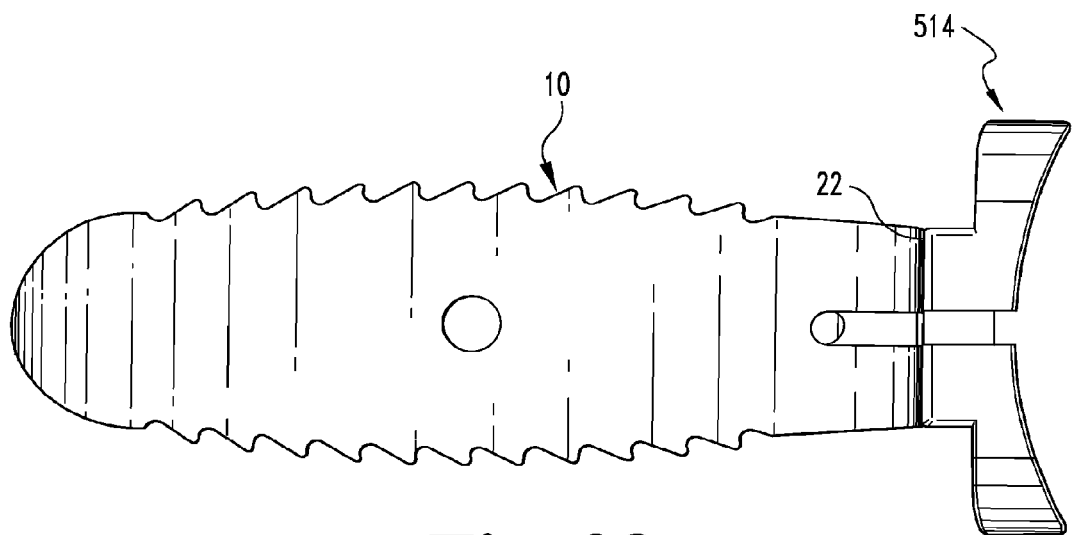
FIG. 28 is an elevation view of the plate of FIG. 27 attached to an interbody implant.
Figure 27:
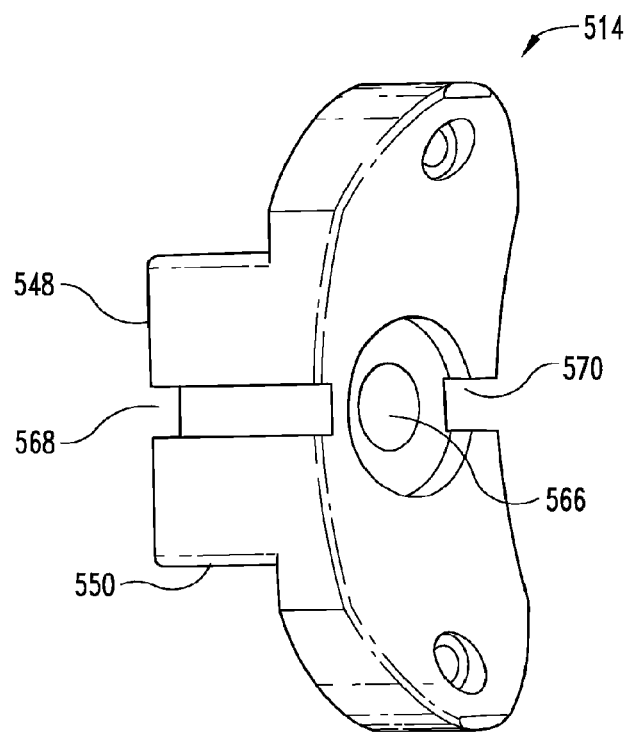
FIG. 27 is a perspective view of another embodiment plate.
Figure 30:
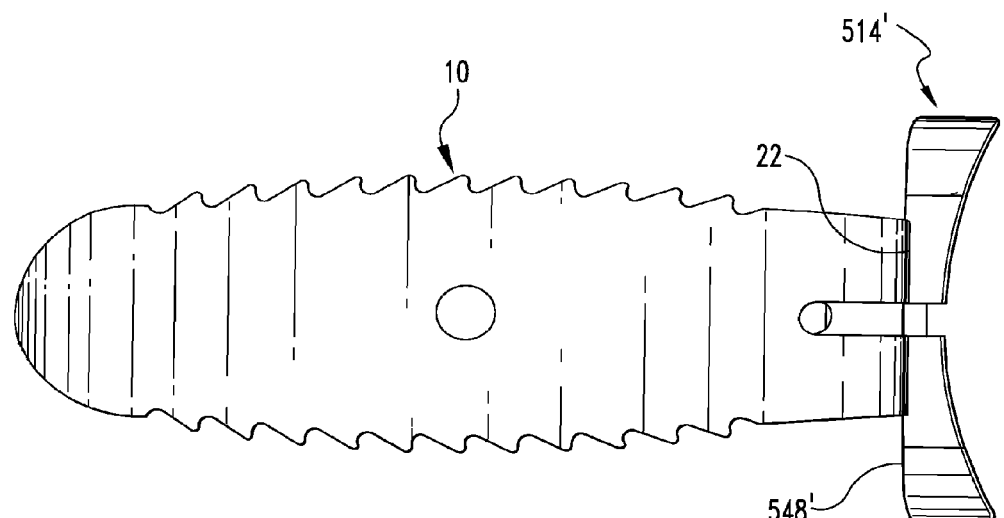
FIG. 30 is an elevation view of the plate of FIG. 29 attached to an interbody implant.
Figure 29:
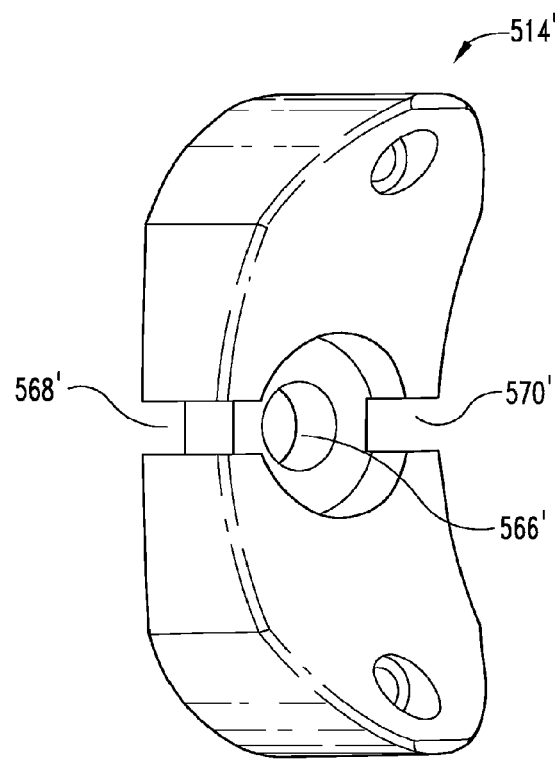
FIG. 29 is a perspective view of another embodiment plate.
Figure 32:
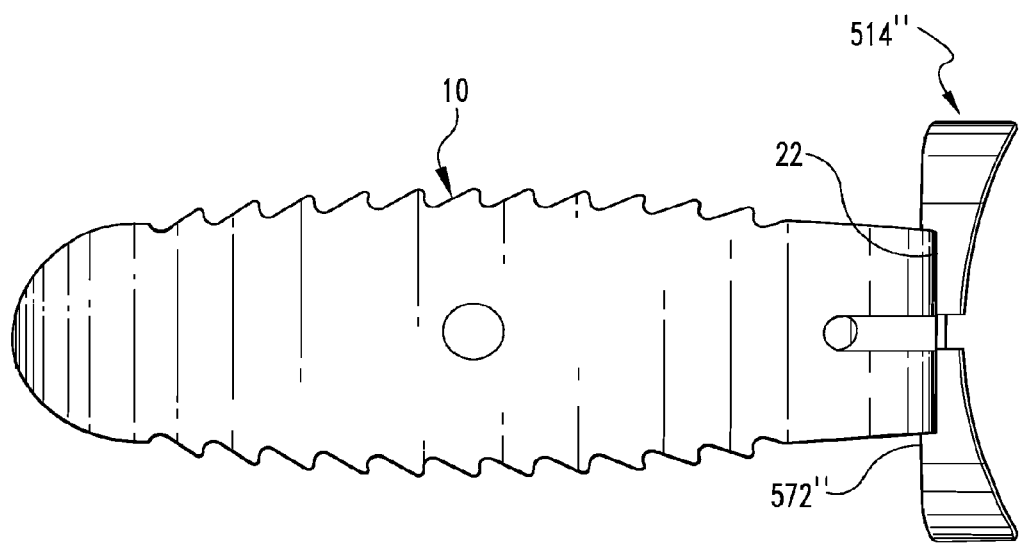
FIG. 32 is an elevation view of the plate of FIG. 31 attached to an interbody implant.
Figure 31:
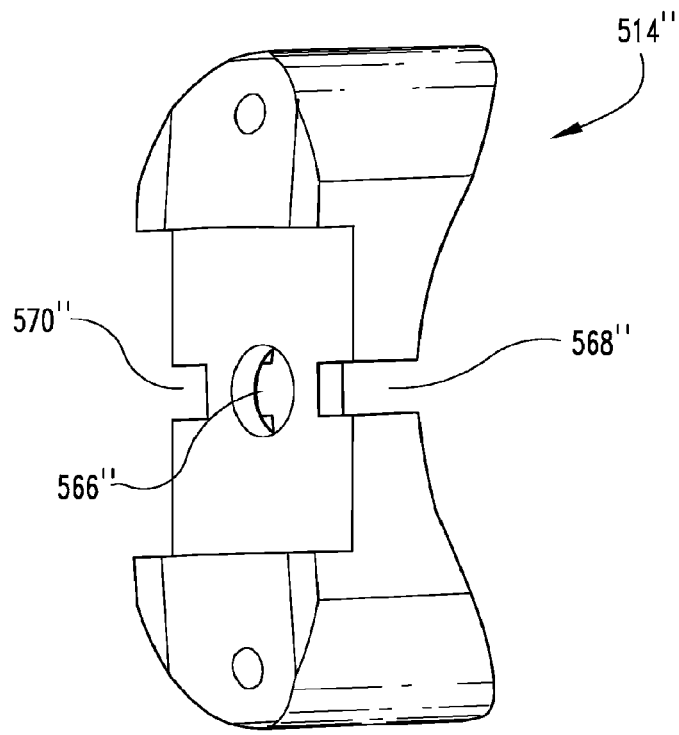
FIG. 31 is a perspective view of another embodiment plate.

FIGS. 27, 29 and 31 show plate embodiments 514, 514' and 514" that are similar to plate embodiments 414, 414' and 414", respectively, but lack tines 452, 454 projecting distally from the opposite sides thereof. In contrast, plates 514, 514', 514" include grooves 568 and 570, grooves 568' and 570', and grooves 568" and 570", respectively, on the opposite sides thereof to receive tines from inserter 100', such as shown with respect to plate 214. In addition, plates 514, 514', 514" each include a central bore 566, 566', 566" to receive a fastener 74 to secure the plate to the trailing end 22 of implant 10. FIGS. 28, 30, and 32 shown plates 514, 514', 514" attached to trailing end 22 of implant 10. In FIG. 28, plate 514 is configured with a monolithic projecting portion 550 to form a spacer to allow engagement of the bottom surface 548 against trailing end 22 when implant 10 with trailing end 22 is recessed relative to the laterally facing surface of the vertebral bodies V1, V2. In FIG. 30, plate 514' is configured with a planar bottom surface 548' for engagement against trailing end 22 when implant 10 is placed with trailing end 22 flush relative to the laterally facing surface of the vertebral bodies V1, V2. In FIG. 32, plate 514" is configured with a notch 572" to receive trailing end 22 when implant 10 is placed with trailing end 22 in overhanging relation to the laterally facing surface of the vertebral bodies V1, V2.

Figure 33:
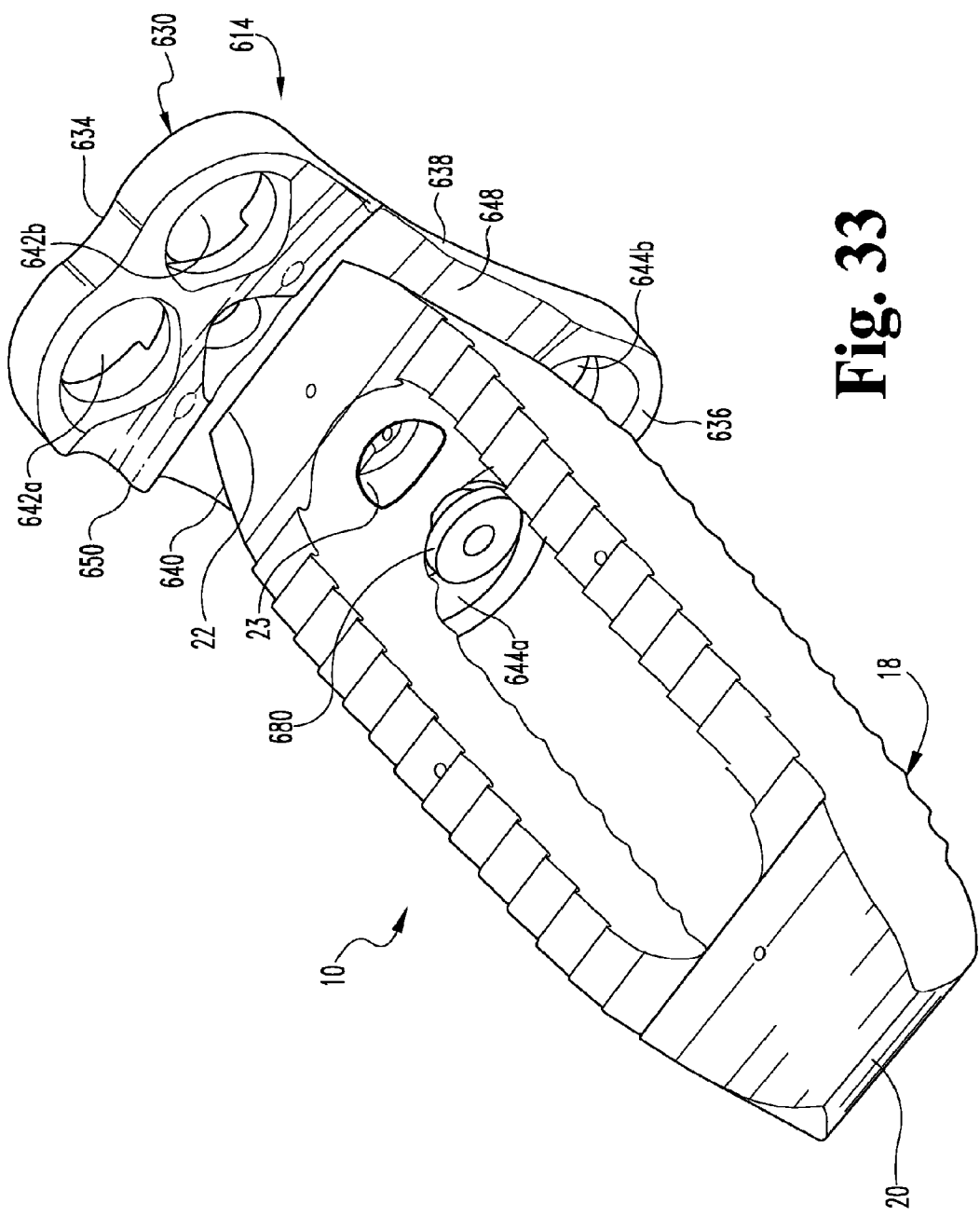
FIG. 33 is a perspective view of another embodiment plate attached to an interbody implant.
Figure 34:
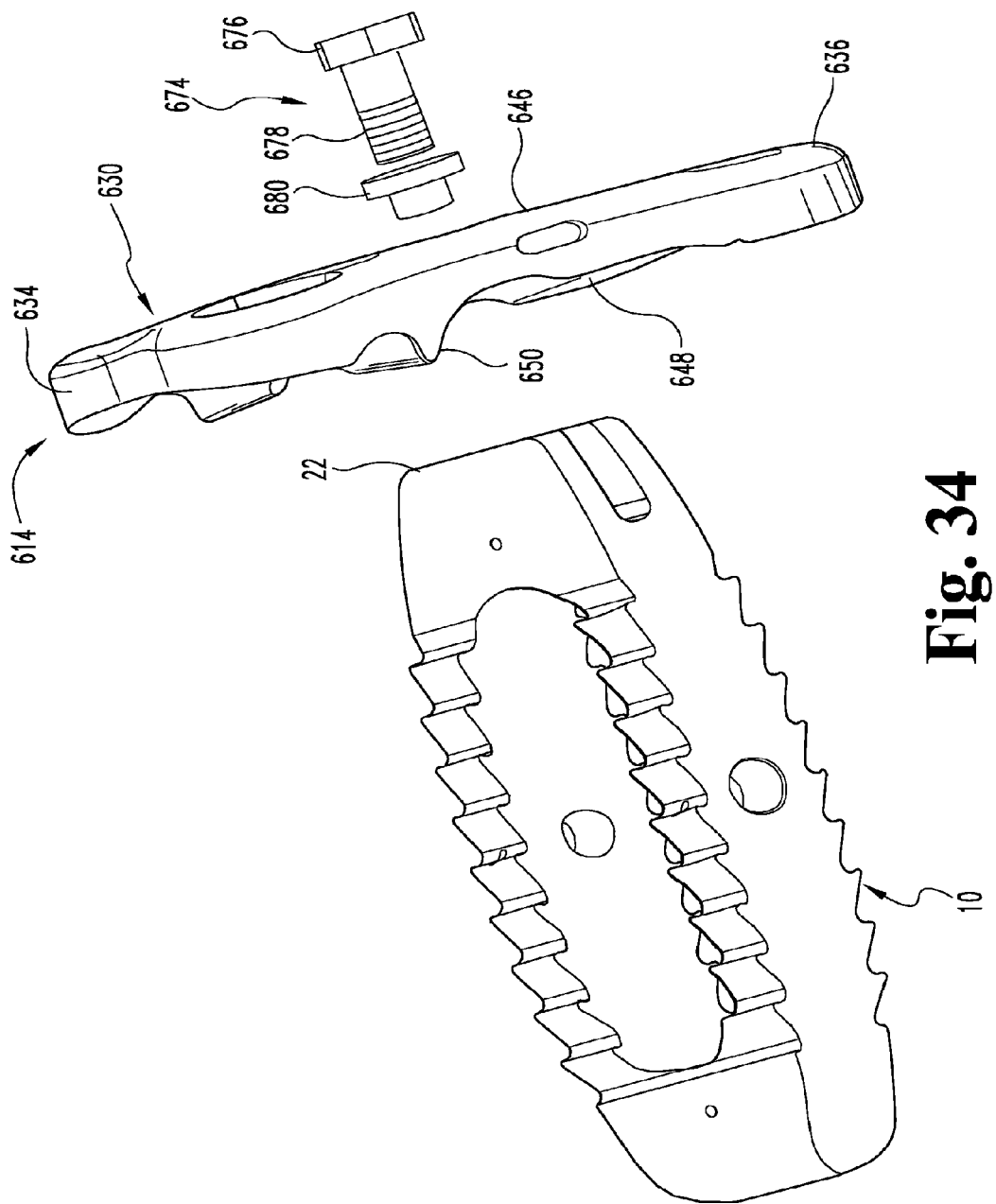
FIG. 34 is an exploded perspective view of the plate and interbody implant of FIG. 41.

Referring to FIG. 33, there is shown implant 10 with another embodiment plate 614 attached to trailing end 22. As further shown in FIG. 34, plate 614 includes a rectangularly shaped body 630 extending between upper end 634 and lower end 636 and opposite sides 638, 640. The size and shape of plate 614 allows a pair of upper bone screw holes 642a, 642b adjacent upper end 634 and a pair of lower bone screw holes 644a, 644b adjacent to lower end 636. Plate 614 also includes a top surface 646 and opposite bottom surface 648 that is positioned in abutting engagement with trailing end 22 of implant 10. Bottom surface 648 includes a ridge 650 extending distally therefrom and between sides 638, 640 that resides against the lateral margin of vertebra V2 between its endplate and its laterally facing surface. Furthermore, plate 614 is attached to implant 10 with fastener 674 extending through a central bore of plate 614 and into receptacle 23 at trailing end 22 of implant 10. Fastener 674 includes a proximal head 676 and a shaft 678 extending distally from head 676. Shaft 678 includes threads extending proximally from the distal end of shaft 678. An end cap 680 is positioned in implant 10 in alignment with receptacle 23, and threadingly receives shaft 678 to secure plate 614 to implant 10.

Figure 35:
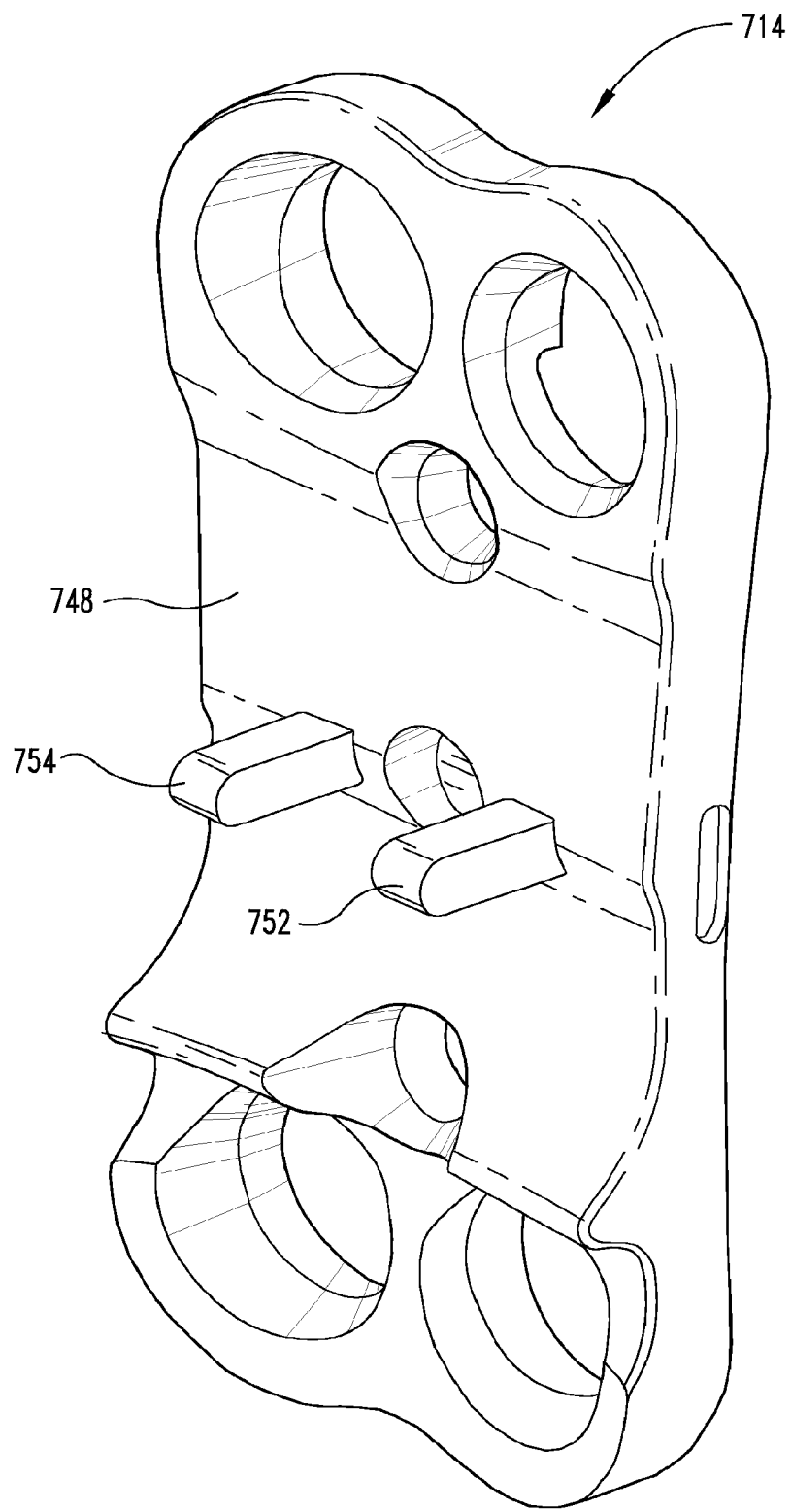
FIG. 35 is a perspective view looking toward the bottom surface of another embodiment plate.
Figure 36:
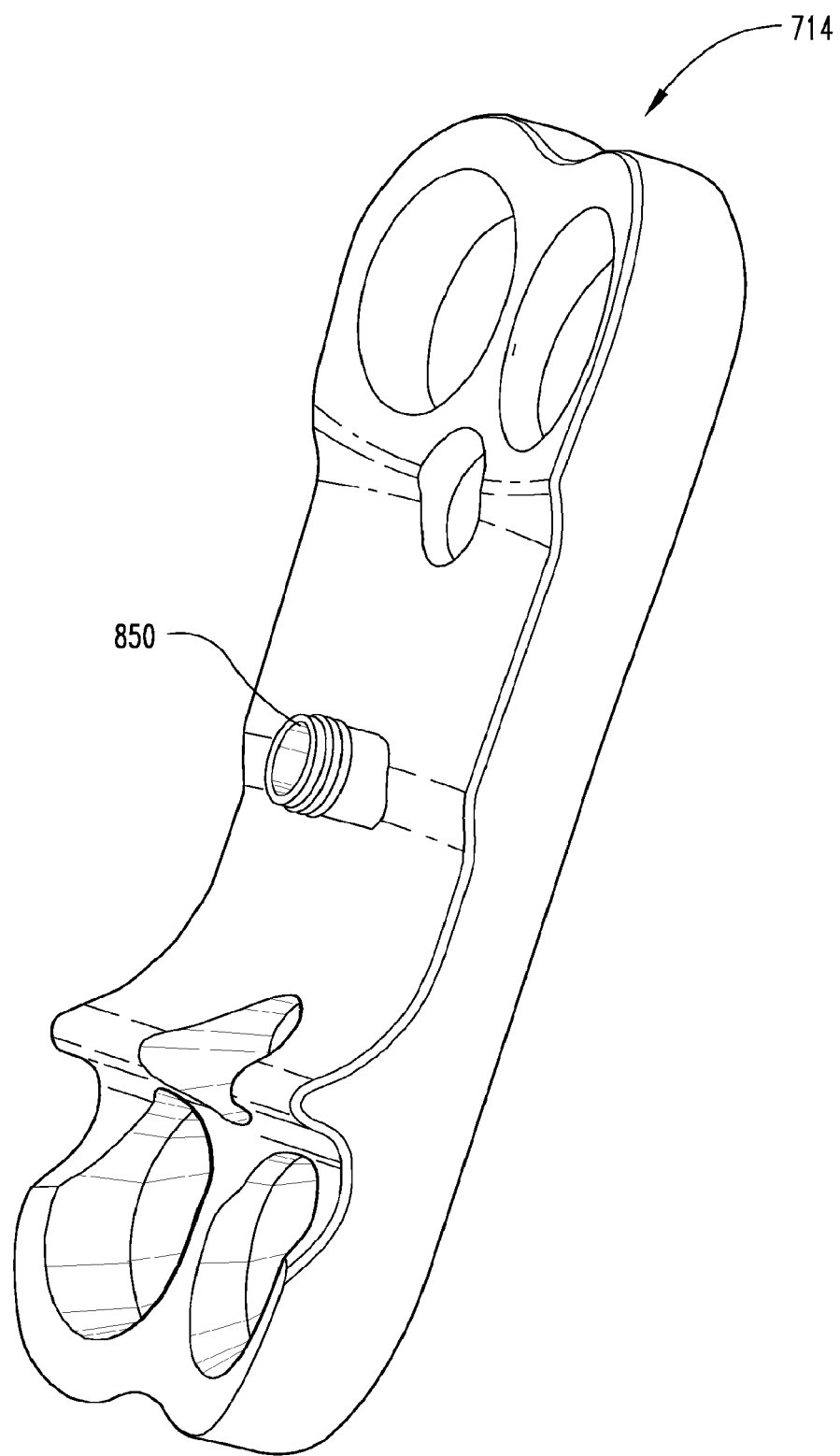
FIG. 36 is a perspective view looking toward the bottom surface of another embodiment plate.

FIG. 35 shows another embodiment plate 714 that is similar to plate 614, except plate 614 includes tines 752, 754 projecting distally outwardly from bottom surface 748. Tines 752, 754 are received in grooves on the opposite sides of, if employed, a spacer, and/or into grooves along the sides of implant 10. In FIG. 36, another embodiment plate 814 is shown that is similar to plate 614, but it includes a central sleeve-shaped projection 850 formed monolithically with plate 814 with threads around the distal end of projection 850. Projection 850 is threadingly engaged to a receptacle in the trailing end 22 of implant 10, eliminating a separate fastener to secure the plate and, if employed, a spacer to the implant.

Figure 37:
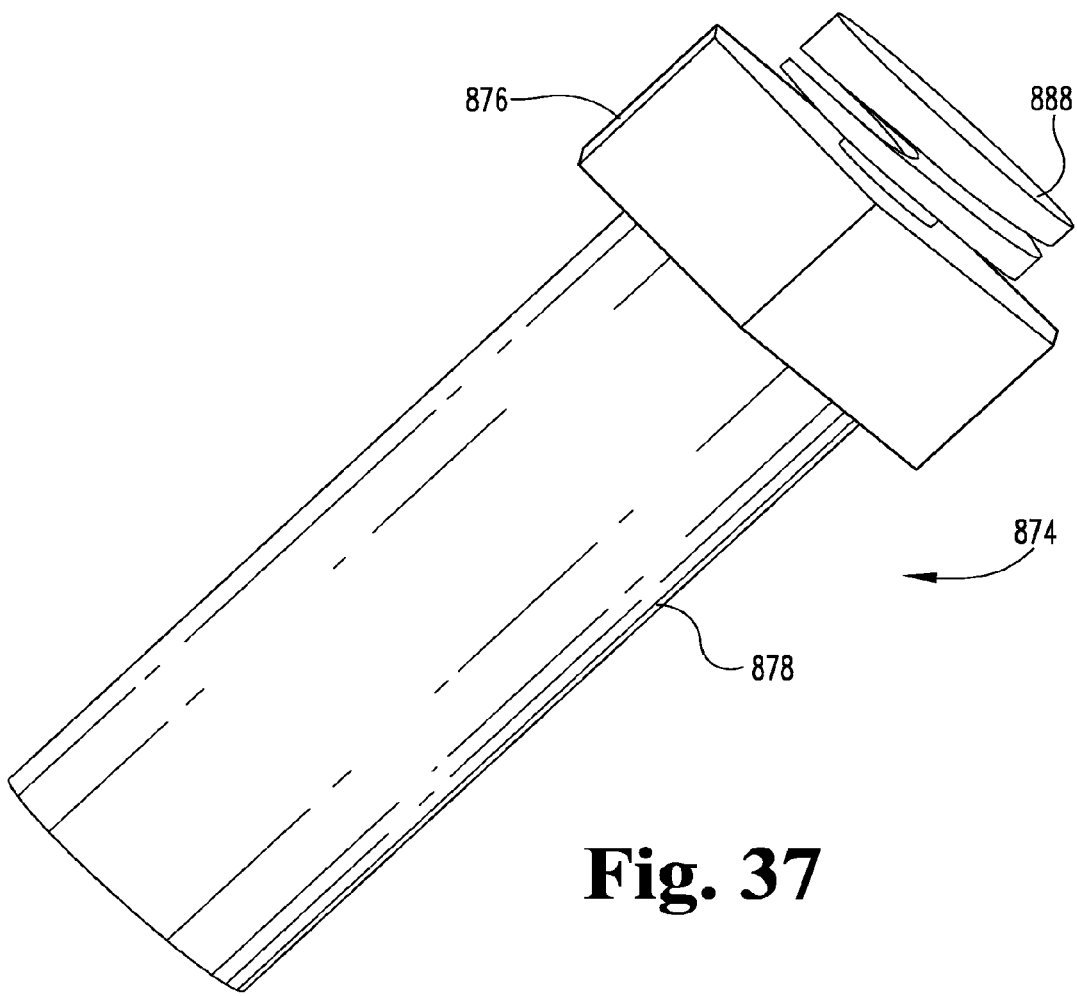
FIG. 37 is a perspective view of another embodiment fastener for securing the plate to an interbody implant.

FIG. 37 shows another embodiment fastener 874 for securing the plate and, if employed, a spacer to implant 10. Fastener 874 includes a proximal head 876 and a shaft 878 extending distally from head 876. Shaft 878 can be smooth, threaded or otherwise configured for engagement to implant 10. Head 876 includes a mounting structure 888 extending proximally therefrom to which an inserter instrument can be mounted to insert that plate and implant assembly into the disc space. The mounting structure can include, for example, a helical groove, internal and/or external threads, a bayonet lock, a friction fit, or clamp fit with the inserter so that the inserter grips the fastener to insert the plate and interbody implant assembly into the patient.

Materials for the implants, plates, and spacers disclosed herein can be chosen from any suitable biocompatible material, such as titanium, titanium alloys, cobalt-chromium, cobalt-chromium alloys, PEEK, PEKK, carbon fiber reinforced PEEK, carbon fiber reinforced PEKK, or other suitable metal or non-metal biocompatible material. The implants, plates and spacers made from the same material, or of different material. Of course, it is understood that the relative size of the components can be modified for the particular vertebra(e) to be instrumented and for the particular location or structure of the vertebrae to which the anchor assembly will be engaged.

Although various embodiments have been described as having particular features and/or combinations of components, other embodiments are possible having a combination of any features and/or components from any of embodiments as discussed above. As used in this specification, the singular forms "a," "an" and "the" include plural referents unless the context clearly dictates otherwise. Thus, for example, the term "a member" is intended to mean a single member or a combination of members, "a material" is intended to mean one or more materials, or a combination thereof. Furthermore, the terms "proximal" and "distal" refer to the direction closer to and away from, respectively, an operator (e.g., surgeon, physician, nurse, technician, etc.) who would insert the medical implant and/or instruments into the patient. For example, the portion of a medical instrument first inserted inside the patient's body would be the distal portion, while the opposite portion of the medical device (e.g., the portion of the medical device closest to the operator) would be the proximal portion.

While the invention has been illustrated and described in detail in the drawings and foregoing description, the same is to be considered as illustrative and not restrictive in character, it being understood that all changes and modifications that come within the spirit of the invention are desired to be protected.

What is claimed is:

1. A method for engaging an implant assembly to a spinal column, comprising:
    attaching a plate to a trailing end of an implant such that a spacer is positioned between the plate and the trailing end of the implant, the implant including a body extending from the trailing end to an opposite leading end, the body including a superior bone engaging surface and an opposite inferior bone engaging surface extending between the leading and trailing ends;
    engaging an inserter instrument to the plate;
    inserting the leading end of the implant in a spinal disc space between first and second vertebrae with the inserter while the spacer is positioned between the plate and the trailing end of the implant;
    advancing the implant into the disc space until a bottom surface of the plate contacts laterally facing surfaces of the first and second vertebrae; and
    engaging the plate to the first and second vertebrae with first and second fasteners.

2. The method of claim 1, wherein the bottom surface of the plate includes a notch extending proximally therein toward a top surface of the plate, a portion of the spacer being positioned in the notch, the notch defining a height along a central longitudinal axis of the plate that extends from an upper end of the plate to an opposite lower end of the plate, the height of the notch being at least as great as a height of the trailing end of the implant from the superior bone engaging surface to the inferior bone engaging surface of the body of the implant.

3. The method of claim 2, wherein attaching the trailing end of the implant to the plate includes attaching the trailing end of the implant in abutting engagement with a distally facing surface of the spacer and attaching a proximally facing surface of the spacer in the notch in abutting engagement with the bottom surface of the plate, wherein the width of the implant extends from the distally facing surface to the proximally facing surface of the spacer.

4. The method of claim 3, wherein when the implant is advanced to contact the laterally facing surfaces of the first and second vertebrae with the bottom surface of the plate, the trailing end of the implant is positioned in one of a flush position and recessed position relative to the laterally facing surfaces of the first and second vertebrae.

5. The method of claim 1, wherein:
the plate includes a top surface opposite the bottom surface, the top and bottom surfaces extending from an upper end to an opposite lower end of the plate, the plate further including opposite sides extending between the top and bottom surfaces and a groove in each of sides, each groove opening at the top surface of the plate and terminating at a distal end located proximally of the bottom surface of the plate; and
engaging the inserter instrument to the plate includes engaging the inserter instrument in the grooves at the opposite sides of the plate.

6. The method of claim 5, wherein engaging the inserter includes inserting a first and a second tine extending distally from the inserter into the grooves of the plate.

7. The method of claim 5, wherein engaging the inserter includes inserting a first and a second tine extending distally from the inserter into the grooves of the plate and into grooves disposed in the body being aligned with the grooves of the plate.

8. The method of claim 1, wherein:
the plate includes a top surface opposite the bottom surface, the top and bottom surfaces extending from an upper end to an opposite lower end of the plate, the plate further including opposite sides extending between the top and bottom surfaces and a groove in each of sides, each groove opening at the top surface of the plate and terminating at a distal end located proximally of the bottom surface of the plate; and
engaging the inserter instrument to the plate includes engaging the inserter instrument in the grooves at the opposite sides of the plate.

9. The method of claim 8, wherein engaging the inserter includes inserting a first and a second tine extending distally from the inserter into the grooves of the plate.

10. The method of claim 1, wherein attaching the plate to the trailing end of the implant comprises inserting a fastener through a central bore in the plate and a central hole in the spacer and into a threaded opening in the trailing end of the implant such that threads on the fastener engage the threaded opening to fix the spacer and the plate relative to the implant.

11. A method for engaging an implant assembly to a spinal column, comprising:
attaching a plate to a trailing end of an implant such that a spacer is positioned between the plate and the trailing end of the implant, the implant including a body extending from the trailing end to an opposite leading end, the body including a superior bone engaging surface and an opposite inferior bone engaging surface extending between the leading and trailing ends;
engaging an inserter instrument to the plate;
inserting the leading end of the implant in a spinal disc space between first and second vertebrae with the inserter while the spacer is positioned between the plate and the trailing end of the implant;
advancing the implant into the disc space until a bottom surface of the plate contacts laterally facing surfaces of the first and second vertebrae and the trailing end of the implant is in an overhanging position; and
engaging the plate to the first and second vertebrae with first and second fasteners.

12. The method of claim 11, further comprising engaging a pair of tines disposed on the inserter with through grooves disposed in the plate and into aligned grooves formed on sides of the implant.

* * * * *